(12) United States Patent
Li et al.

(10) Patent No.: US 8,618,133 B2
(45) Date of Patent: Dec. 31, 2013

(54) ARALKYL ALCOHOL PYRIDINE DERIVATIVE COMPOUNDS AND THE USE THEREOF AS MEDICAMENTS FOR TREATING DEPRESSION

(75) Inventors: Jianqi Li, Shanghai (CN); Kai Gao, Jiangsu province (CN); Wangping Cai, Jiangsu province (CN); Yongyong Zheng, Shanghai (CN)

(73) Assignee: Jiangsu Hengyi Pharmaceutical Co., Ltd., Nanjing, Jiangsu Province (CN)

( * ) Notice: Subject to any disclaimer, the term of this patent is extended or adjusted under 35 U.S.C. 154(b) by 145 days.

(21) Appl. No.: 12/997,511

(22) PCT Filed: Jun. 8, 2009

(86) PCT No.: PCT/CN2009/072171
§ 371 (c)(1),
(2), (4) Date: Mar. 9, 2011

(87) PCT Pub. No.: WO2009/149649
PCT Pub. Date: Dec. 17, 2009

(65) Prior Publication Data
US 2011/0160247 A1   Jun. 30, 2011

(30) Foreign Application Priority Data
Jun. 10, 2008   (CN) .......................... 2008 1 0038745

(51) Int. Cl.
*A61K 31/445* (2006.01)
*C07D 211/18* (2006.01)

(52) U.S. Cl.
USPC ............................ 514/319; 546/205; 546/206

(58) Field of Classification Search
USPC .................................. 514/319; 546/205, 206
See application file for complete search history.

(56) References Cited

U.S. PATENT DOCUMENTS

| | | | |
|---|---|---|---|
| 4,921,863 A * | 5/1990 | Sugimoto et al. | 514/319 |
| 6,787,560 B2 * | 9/2004 | Kodo et al. | 514/331 |
| 2001/0039286 A1 | 11/2001 | Dinnell et al. | |
| 2003/0191126 A1 | 10/2003 | Kodo et al. | |

FOREIGN PATENT DOCUMENTS

| | | |
|---|---|---|
| CN | 1384102 | 11/2002 |
| WO | 8802365 | 7/1988 |

OTHER PUBLICATIONS

Archibale "Antiinflammatory . . . " CA77:34355 (1972).*
Archibald et al. "Benzamidopiperidines . . . " CA81:114406 (1974).*
Braga et al. "Malong crstals . . . " J. Roy. Soc. Chem. Chem. Commu. p. 3635-3645 (2005).*
Cavalla et al. CA84:43866 (1976).*
Improper Markush, p. 1, 64-66 (2011).*
Karibe et al. "Preparation of . . . " CA115:8586 (1991).*
Kodo et al. "Piperidine . . . " CA148:495798 (2008).*
Patani et al. "Bioisosterism . . . " Chem. Rev. v.96, p. 3147-3176 (1996).*
Picciola et al. "Preparation of bicyclic . . . " CA107:211871 (1987).*
Rubini et al. "Synthesis of isosteric . . . " Tetrhedron v.42(21) p. 6039-6045 (1986).*
Seddon "Pseudopolymorph . . . " Cryst. Growth & design v.4(6) p. 1847 (2004).*
Sugimoto et al. "preparation of N-containing . . . " CA110:57520 (1989).*
International Search Report for PCT/CN2009/072171 dated Sep. 2, 2009.

* cited by examiner

*Primary Examiner* — Celia Chang
(74) *Attorney, Agent, or Firm* — Andrus, Sceales, Starke & Sawall, LLP

(57) ABSTRACT

The present invention relates to an aralkyl alcohol piperidine derivative and use as antidepressant thereof. The said aralkyl alcohol piperidine derivative has a triple inhibition effect on the reuptaking of 5-HT, NA and DA. The derivative may be administered to the patient in need of such treatment in the form of composition by oral administration, injection and the like. The derivative is a compound having the following general formula or its salt:

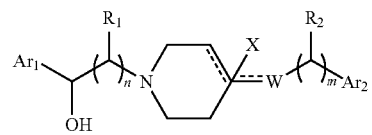

5 Claims, No Drawings

ARALKYL ALCOHOL PYRIDINE DERIVATIVE COMPOUNDS AND THE USE THEREOF AS MEDICAMENTS FOR TREATING DEPRESSION

CROSS-REFERENCE TO RELATED APPLICATIONS

This application is the U.S. national stage application of International Application PCT/CN2009/072171, filed Jun. 8, 2009, which international application was published on Dec. 17, 2009, as International Publication WO2009/149649A1 in the Chinese language. The International Application claims priority of Chinese Patent Application No. 200810038745.1 filed Jun. 10, 2008.

TECHNICAL FIELD

The present invention relates to an aralkyl alcohol piperidine derivative and the use as an antidepressant thereof.

BACKGROUND ART

Depression is the most common mental disorder that threatens human physical and mental health and has a morbidity of about 5% of the world population. The disease severely affects human health and living quality and is expected to become the second largest disease threatening human health and shortening human life to the year 2020.

The mechanism of antidepressant has not been elucidated up to now. Medicament having obvious treatment effect acts essentially on synapse parts of nerve endings, and plays role by modulating level of neurotransmitter of synapse gaps. Studies on the biochemical of the etiology show that depression is mainly related to five neurotransmitters such as central 5-hydroxytryptamine (5-HT), norepinephrine (NA), dopamine (DA), acetylcholine (Ach) and γ-aminobutyric acid (GABA), etc.

Antidepressants can be classified to two major groups: the early non-selective antidepressants and the novel selective reuptake inhibitors. The non-selective antidepressants include mainly monoamine oxidase inhibitors (MAOIs) and tricyclic antidepressants (TCAs); and selective reuptake inhibitors mainly include (1) selective serotonin (5-HT) reuptake inhibitors (SSRIs) such as fluoxetine and paroxetine, (2) norepinephrine (NA) reuptake inhibitors (NDRIs) such as Reboxitine, (3) norepinephrine-dopamine and specificity 5-HT reuptake inhibitors (NDRIs) such as Mirtazapine, (4) 5-HT and NA reuptake inhibitor (SNRIs) such as Venlafaxine and Duloxetine, and (5) selective serotonin reuptake enhancers (SSREs) such as Tianeptine, etc.

Although a large number of antidepressants are used clinically for treating depression, the treatment is ineffective to many patients and electric convulsive treatment is needed since some medicaments are in low response rate and have possible side effects. Therefore, the development of antidepressants is still the point for the study and research of new medicament and large amount of investment are involved to develop new drugs in many pharmaceutical manufactures.

The current research trends of the development of antidepressant are focused on the following two points: The first is the secondary development of the existing medicaments, including: 1) further developing new indications of the existing medicaments; and 2) changing dosage forms of the existing medicaments.

The second is to further develop new products, which is to develop novel medicaments having better and more prompt effects and safer for treating depression than those commercially available currently by finding compounds that act on new target or multiple targets and have new structural type.

Patent WO88/02365 discloses an aralkyl alcohol piperidine derivative for treatment of cerebrovascular disease.

On the research of new antidepressant, many attentions are focused on the study of the triple reuptake inhibitor currently, which hopefully will solve the problem of delayed effect on the existing antidepressants, and will improve the effectiveness and safety. The triple Reuptake inhibitors, also named as "broad spectrum" antidepressants, refers to compounds that can inhibit the reuptake of three monoamine transporters, i.e. 5-HT, NA and DA that are closely related to depression simultaneously.

The triple reuptake antidepressant is still on the stage of clinical research at the moment. For example, the triple Reuptake inhibitor DOV-216303 developed by DOV Pharmaceutical is on the clinical III-stage, and NS-2359 co-developed by GSK and NeuroSearch is on anti-depression clinical II-stage. These monoamine transporter triple-reuptake antidepressants are advantageous in potent and prompt efficiency, and have become the emphasis in the anti-depression field. The development and research of new antidepressants in China is in the preliminary stage, particularly studies on new antidepressants that acts on three systems: 5-HT, NA and DA, and is an important theme.

CONTENTS OF THE INVENTION

One of the objects of the present invention is to disclose a group of aralkyl alcohol piperidine derivatives to overcome the defects of slow onset, low efficiency, great side-effects and less safety and to meet the requirements for the treatment of depression in humans.

The second object of the present invention is to disclose use of the above derivative as a medicament for treating depression.

The alkyl alcohol piperazine derivative of the present invention is a compound of the following structural formulae or a free base or a salt thereof, the said salt is hydrochloride, hydrobromide, sulfate, trifluoroacetate or methanesulfonate, etc., preferably hydrochloride, hydrobromide, wherein the salt contains 0.5-3 molecules of crystal water:

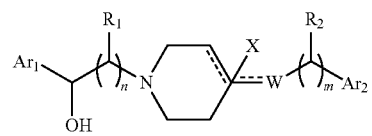

wherein:

$Ar_1$ represents:

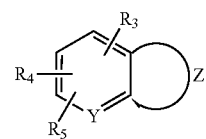

Ar₁ represents:

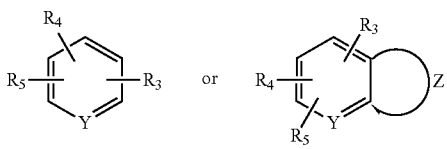

R₁ represents one of hydrogen, $C_1$-$C_5$ alkyl; halogenated $C_1$-$C_5$ alkyl, $C_5$ alicyclic ring or $C_6$ alicyclic ring, phenyl or substituted phenyl;
R₂ represents one of hydrogen, $C_1$-$C_5$ alkyl, halogenated $C_1$-$C_5$ alkyl, $C_5$ alicyclic ring or $C_6$ alicyclic ring, phenyl or substituted phenyl;
R₃, R₄, and R₅ each represents one of hydrogen, $C_1$-$C_3$ alkyl, halogenated $C_1$-$C_3$ alkyl, $C_5$ alicyclic ring, $C_6$ alicyclic ring, phenyl, substituted phenyl, hydroxyl, methoxy, ethoxy, amino, substituted amino, halogen, carboxylic acid, carboxylic ester, nitro or acetonitrile;
W represents C, N, or O;
X represents hydrogen, hydroxyl, or $C_1$-$C_3$ alkoxy;
Y represents C, or N;
Z represents a live-member or six-member ring containing C, S, N, or O;
n=1, 2, 3; m=0, 1, 2, 3;
----- represents single or double bonds;
The asymmetric carbon in the structure is non-chiral and chiral carbon atom;
The said substituted phenyl group is phenyl ring having 1 to 4 substituents, wherein the substituents are halogen, hydroxyl, alkoxy or amino group.
The said substituted amino is amino containing $C_1$-$C_3$ alkyl or halogenated $C_1$-$C_3$ alkyl.
wherein:
(1) when R₁ represents hydrogen, ----- represents hydrogen, W represents single bond, W represents C, m=0, Ar₂ is not:

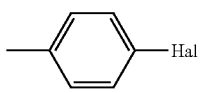

wherein Hal is halogen;
(2) when R₁ represents hydrogen, X represents hydrogen, ----- represents exocyclic double bond, W represents C, m=0, Ar₂ is not:

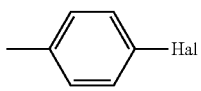

wherein Hal is halogen;
The preferable compounds of the present invention include:
V-1 Threo-4-benzyl-N-[1-methyl-2-hydroxy-2-(5-chloro-6-methoxynaphthalene-2-yl)]ethylpiperidine;
V-2 Erythro-4-benzyl-N-[1-methyl-2-hydroxy-2-(5-chloro-6-methoxynaphthalene-2-yl)]ethylpiperidine;
V-3 Threo-4-benzyl-N-[1-methyl-2-hydroxy-2-(benzothiophene-3-yl)]ethylpiperidine;
V-4 Erythro-4-benzyl-N-[1-methyl-2-hydroxy-2-(benzothiophene-3-yl)]ethylpiperidine;
V-5 Threo-4-benzyl-N-[1-ethyl-2-hydroxy-2-(5-chloro-6-methoxynaphthalene-2-yl)]ethylpiperidine;
V-6 Erythro-4-benzyl-N-[1-ethyl-2-hydroxy-2-(5-chloro-6-methoxynaphthalene-2-yl)]ethylpiperidine;
V-7 4-benzyl-N-[2-hydroxy-2-(5-chloro-6-methoxynaphthalene-2-yl)]ethylpiperidine;
V-8 4-benzyl-N-[2-hydroxy-2-(benzothiophene-3-yl)]ethylpiperidine;
V-9 4-benzyl-N-[3-hydroxy-3-(5-chloro-6-methoxynaphthalene-2-yl)]propylpiperidine;
V-10 4-benzyl-N-[3-hydroxy-3-(benzothiophene-3-yl)]propylpiperidine;
V-11 Threo-4-(4-fluorobenzyl)-N-[1-methyl-2-hydroxy-2-(5-chloro-6-methoxynaphthalene-2-yl)]ethylpiperidine;
V-12 Erythro-4-(4-fluorobenzyl)-N-[1-methyl-2-hydroxy-2-(5-chloro-6-methoxynaphthalene-2-yl)]ethylpiperidine;
V-13 Threo-4-benzyl-4-hydroxy-N-[1-methyl-2-hydroxy-2-(5-chloro-6-methoxynaphthalene-2-yl)]ethylpiperidine;
V-14 Erythro-4-benzyl-4-hydroxy-N-[1-methyl-2-hydroxy-2-(5-chloro-6-methoxynaphthalene-2-yl)]ethylpiperidine;
V-15 Threo-4-benzyl-4-hydroxy-N-[1-ethyl-2-hydroxy-2-(5-chloro-6-methoxynaphthalene-2-yl)]ethylpiperidine;
V-16 Erythro-4-benzyl-4-hydroxy-N-[1-ethyl-2-hydroxy-2-(5-chloro-6-methoxynaphthalene-2-yl)]ethylpiperidine;
V-17 Threo-4-benzyl-4-hydroxy-N-[1-ethyl-2-hydroxy-2-(benzothiophene-3-yl)]ethylpiperidine;
V-18 Erythro-4-benzyl-4-hydroxy-N-[1-ethyl-2-hydroxy-2-(benzothiophene-3-yl)]ethylpiperidine;
V-19 4-benzyl-4-hydroxy-N-[2-hydroxy-2-(5-chloro-6-methoxynaphthalene-2-yl)]ethylpiperidine;
V-20 4-benzyl-4-hydroxy-N-[3-hydroxy-3-(5-chloro-6-methoxynaphthalene-2-yl)]propylpiperidine;
V-21 Threo-4-(4-chlorobenzyl)-4-hydroxy-N-[1-methyl-2-hydroxy-2-(5-chloro-6-methoxynaphthalene-2-yl)]ethylpiperidine;
V-22 4-(4-chlorobenzyl)-4-hydroxy-N-[1-methyl-2-hydroxy-2-(5-chloro-6-methoxynaphthalene-2-yl)]ethylpiperidine;
V-23 Threo-4-(4-fluorobenzyl)-4-hydroxy-N-[1-methyl-2-hydroxy-2-(5-chloro-6-methoxynaphthalene-2-yl)]ethylpiperidine;
V-24 Erythro-4-(4-fluorobenzyl)-4-hydroxy-N-[1-methyl-2-hydroxy-2-(5-chloro-6-methoxynaphthalene-2-yl)]ethylpiperidine;
V-25 Threo-4-(3,4-dichlorobenzyl)-methylene-N-[1-methyl-2-hydroxy-2-(5-chloro-6-methoxynaphthalene-2-yl)]ethylpiperidine;
V-26 Erythro-4-(3,4-dichlorobenzyl)-methylene-N-[1-methyl-2-hydroxy-2-(5-chloro-6-methoxynaphthalene-2-yl)]ethylpiperidine;
V-27 Threo-4-benzyl-methylene-N-[1-methyl-2-hydroxy-2-(benzothiophene-3-yl)]ethylpiperidine;
V-28 Erythro-4-benzyl-methylene-N-[1-methyl-2-hydroxy-2-(benzothiophene-3-yl)]ethylpiperidine;
V-29 Threo-4-(3,4-dichlorobenzyl)-methylene-N-[1-ethyl-2-hydroxy-2-(5-chloro-6-methoxynaphthalene-2-yl)]ethylpiperidine;
V-30 4-(3,4-dichlorobenzyl)-methylene-N-[1-ethyl-2-hydroxy-2-(5-chloro-6-methoxynaphthalene-2-yl)]ethylpiperidine;
V-31 4-benzyl-methylene-N-[2-hydroxy-2-(5-chloro-6-methoxynaphthalene-2-yl)]ethylpiperidine;
V-32 4-benzyl-methylene-N-[3-hydroxy-3-(5-chloro-6-methoxynaphthalene-2-yl)]propylpiperidine;
V-33 Threo-4-(4-fluorobenzyl)-methylene-N-[1-ethyl-2-hydroxy-2-(5-chloro-6-methoxynaphthalene-2-yl)]ethylpiperidine;

V-34 Erythro-4-(4-fluorobenzyl)-methylene-N-[1-ethyl-2-hydroxy-2-(5-chloro-6-methoxynaphthalene-2-yl)]ethylpiperidine;
V-35 Threo-4-(4-chlorobenzyl)-methylene-N-[1-ethyl-2-hydroxy-2-(5-chloro-6-methoxynaphthalene-2-yl)]ethylpiperidine;
V-36 Erythro-4-(4-chlorobenzyl)-methylene-N-[1-ethyl-2-hydroxy-2-(5-chloro-6-methoxynaphthalene-2-yl)]ethylpiperidine;
V-37 Threo-4-benzol-methylene-N-[1-ethyl-2-hydroxy-2-(5-chloro-6-methoxynaphthalene-2-yl)]ethylpiperidine;
V-38 Erythro-4-benzyl-methylene-N-[1-ethyl-2-hydroxy-2-(5-chloro-6-methoxynaphthalene-2-yl)]ethylpiperidine;
V-39 Threo-4-benzyl-N-[1-methyl-2-hydroxy-2-(5-chloro-6-methoxynaphthalene-2-yl)]ethyl-1,2,3,6-tetrahydropyridine;
V-40 Erythro-4-benzyl-N-[1-methyl-2-hydroxy-2-(5-chloro-6-methoxynaphthalene-2-yl)]ethyl-1,2,3,6-tetrahydropyridine;
V-41 Threo-4-benzyl-N-[1-methyl-2-hydroxy-2-(benzothiophene-3-yl)]ethyl-1,2,3,6-tetrahydropyridine;
V-42 Erythro-4-benzyl-[1-methyl-2-hydroxy-2-(benzothiophene-3-yl)]ethyl-1,2,3,6-tetrahydropyridine;
V-43 Threo-4-benzyl-N-[1-ethyl-2-hydroxy-2-(5-chloro-6-methoxynaphthalene-2-yl)]ethyl-1,2,3,6-tetrahydropyridine;
V-44 Erythro-4-benzyl-N-[1-ethyl-2-hydroxy-2-(5-chloro-6-methoxynaphthalene-2-yl)]ethyl-1,2,3,6-tetrahydropyridine;
V-45 4-benzyl-N-[2-hydroxy-2-(5-chloro-6-methoxynaphthalene-2-yl)]ethyl-1,2,3,6-tetrahydropyridine;
V-46 4-benzyl-N-[3-hydroxy-3-(5-chloro-6-methoxynaphthalene-2-yl)]propyl-1,2,3,6-tetrahydropyridine;
V-47 Threo-4-(4-fluorobenzyl)-N-[1-methyl-2-hydroxy-2-(5-chloro-6-methoxynaphthalene-2-yl)]ethyl-1,2,3,6-tetrahydropyridine;
V-48 Erythro-4-(4-fluorobenzyl)-N-[1-methyl-2-hydroxy-2-(5-chloro-6-methoxynaphthalene-2-yl)]ethyl-1,2,3,6-tetrahydropyridine;
V-49 Threo-4-benzyloxy)-N-[1-methyl-2-hydroxy-2-(5-chloro-6-methoxynaphthalene-2-yl)]ethylpiperidine;
V-50 Erythro-4-benzyloxy-N-[1-methyl-2-hydroxy-2-(5-chloro-6-methoxynaphthalene-2-yl)]ethylpiperidine;
V-51 Threo-4-benzyloxy-N-[1-methyl-2-hydroxy-2-(benzothiophene-3-yl)]ethylpiperidine;
V-52 Erythro-4-benzyloxy-N-[1-methyl-2-hydroxy-2-(benzothiophene-3-yl)]ethylpiperidine;
V-53 Threo-4-benzyloxy-N-[1-ethyl-2-hydroxy-2-(5-chloro-6-methoxynaphthalene-2-yl)]ethylpiperidine;
V-54 Erythro-4-benzyloxy-N-[1-ethyl-2-hydroxy-2-(5-chloro-6-methoxynaphthalene-2-yl)]ethylpiperidine;
V-55 4-benzyloxy-N-[2-hydroxy-2-(5-chloro-6-methoxynaphthalene-2-yl)]ethylpiperidine;
V-56 4-benzyloxy-N-[3-hydroxy-3-(5-chloro-6-methoxynaphthalene-2-yl)]propylpiperidine;
V-57 4-benzyloxy-N-[3-hydroxy-2-(benzothiophene-3-yl)]propylpiperidine;
V-58 4-benzyloxy-N-[3-hydroxy-3-(indole-3-yl)]propylpiperidine;
V-59 Threo-4-(4-fluorobenzyloxy)-N-[1-methyl-2-hydroxy-2-(5-chloro-6-methoxynaphthalene-2-yl)]ethylpiperidine;
V-60 Erythro-4-(4-fluorobenzyloxy)-N-[1-methyl-2-hydroxy-2-(5-chloro-6-methoxynaphthalene-2-yl)]ethylpiperidine;
V-61 Threo-4-(4-fluorobenzylamino)-N-[1-methyl-2-hydroxy-2-(5-chloro-6-methoxynaphthalene-2-yl)]ethylpiperidine;
V-62 Erythro-4-(4-fluorobenzylamino)-N-[1-methyl-2-hydroxy-2-(5-chloro-6-methoxynaphthalene-2-yl)]ethylpiperidine or
V-63 4-benzyl-4-methoxy-N-[3-hydroxy-3-(5-chloro-6-methoxynaphthalene-2-yl)]propylpiperidine.

The most preferably compound is V-14: Erythro-4-benzyl-4-hydroxy-N-[1-methyl-2-hydroxy-2-(5-chloro-6-methoxynaphthalene-2-yl)]ethylpiperidine.

The following Table 1 shows the structural formulae of the above compounds:

TABLE 1

| No. | Ar$_1$ | Ar$_2$ | R$_1$ | R$_2$ | n | m | W | X | ----- |
|---|---|---|---|---|---|---|---|---|---|
| V-1 | 2-methoxy-1-chloro-6-methylnaphthalene | Ph | CH$_3$ | H | 1 | 0 | CH$_2$ | H | single bond |
| V-2 | 2-methoxy-1-chloro-6-methylnaphthalene | Ph | CH$_3$ | H | 1 | 0 | CH$_2$ | H | single bond |
| V-3 | 3-methylbenzothiophene | Ph | CH$_3$ | H | 1 | 0 | CH$_2$ | H | single bond |
| V-4 | 3-methylbenzothiophene | Ph | CH$_3$ | H | 1 | 0 | CH$_2$ | H | single bond |

TABLE 1-continued

| No. | Ar$_1$ | Ar$_2$ | R$_1$ | R$_2$ | n | m | W | X | ----- |
|---|---|---|---|---|---|---|---|---|---|
| V-5 | 1-Cl-2-MeO-naphth-6-yl | Ph | CH$_3$CH$_2$ | H | 1 | 0 | CH$_2$ | H | single bond |
| V-6 | 1-Cl-2-MeO-naphth-6-yl | Ph | CH$_3$CH$_2$ | H | 1 | 0 | CH$_2$ | H | single bond |
| V-7 | 1-Cl-2-MeO-naphth-6-yl | Ph | H | H | 1 | 0 | CH$_2$ | H | single bond |
| V-8 | benzo[b]thiophen-3-yl | Ph | CH$_3$ | H | 1 | 0 | CH$_2$ | H | single bond |
| V-9 | 1-Cl-2-MeO-naphth-6-yl | Ph | H | H | 2 | 0 | CH$_2$ | H | single bond |
| V-10 | benzo[b]thiophen-3-yl | Ph | H | H | 2 | 0 | CH$_2$ | H | single bond |
| V-11 | 1-Cl-2-MeO-naphth-6-yl | 4-F-C$_6$H$_4$ | CH$_3$ | H | 1 | 0 | CH$_2$ | H | single bond |
| V-12 | 1-Cl-2-MeO-naphth-6-yl | 4-F-C$_6$H$_4$ | CH$_3$ | H | 1 | 0 | CH$_2$ | H | single bond |
| V-13 | 1-Cl-2-MeO-naphth-6-yl | Ph | CH$_3$ | H | 1 | 0 | CH$_2$ | OH | single bond |
| V-14 | 1-Cl-2-MeO-naphth-6-yl | Ph | CH$_3$ | H | 1 | 0 | CH$_2$ | OH | single bond |

TABLE 1-continued
| No. | Ar$_1$ | Ar$_2$ | R$_1$ | R$_2$ | n | m | W | X | ---- |
|---|---|---|---|---|---|---|---|---|---|
| V-15 | 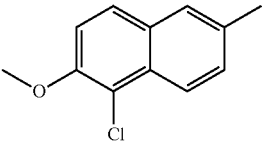 | Ph | CH$_3$CH$_2$ | H | 1 | 0 | CH$_2$ | OH | single bond |
| V-16 | 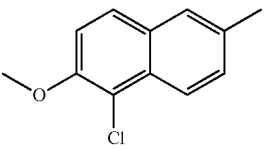 | Ph | CH$_3$CH$_2$ | H | 1 | 0 | CH$_2$ | OH | single bond |
| V-17 | 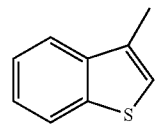 | Ph | CH$_3$CH$_2$ | H | 1 | 0 | CH$_2$ | OH | single bond |
| V-18 | 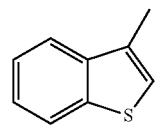 | Ph | CH$_3$CH$_2$ | H | 1 | 0 | CH$_2$ | OH | single bond |
| V-19 | 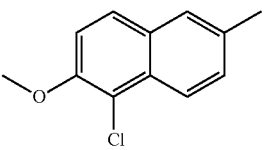 | Ph | H | H | 1 | 0 | CH$_2$ | OH | single bond |
| V-20 | 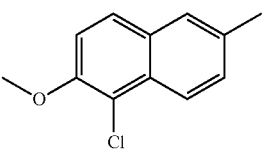 | Ph | H | H | 2 | 0 | CH$_2$ | OH | single bond |
| V-21 | 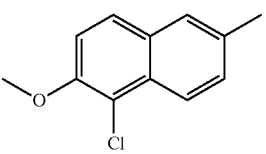 | 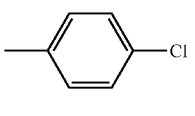 | CH$_3$ | H | 1 | 0 | CH$_2$ | OH | single bond |
| V-22 | 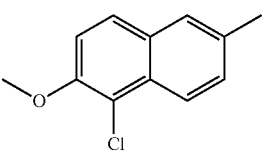 | 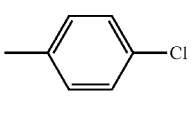 | CH$_3$ | H | 1 | 0 | CH$_2$ | OH | single bond |
| V-23 | 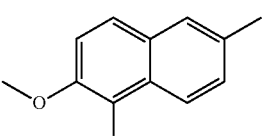 | 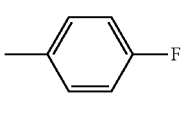 | CH$_3$ | H | 1 | 0 | CH$_2$ | OH | single bond |
| V-24 | 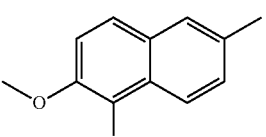 | 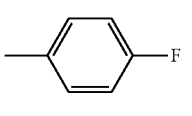 | CH$_3$ | H | 1 | 0 | CH$_2$ | OH | single bond |

TABLE 1-continued

| No. | Ar₁ | Ar₂ | R₁ | R₂ | n | m | W | X | ----- |
|---|---|---|---|---|---|---|---|---|---|
| V-25 | 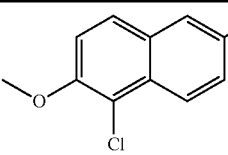 | 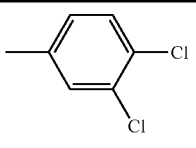 | CH₃ | H | 1 | 0 | CH | H | double bond (exocyclic) |
| V-26 | 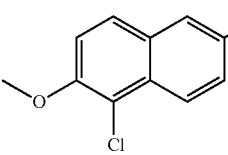 | 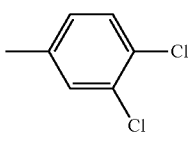 | CH₃ | H | 1 | 0 | CH | H | double bond (exocyclic) |
| V-27 | 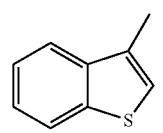 | Ph | CH₃ | H | 1 | 0 | CH | H | double bond (exocyclic) |
| V-28 | 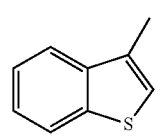 | Ph | CH₃ | H | 1 | 0 | CH | H | double bond (exocyclic) |
| V-29 | 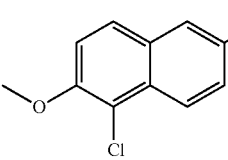 | 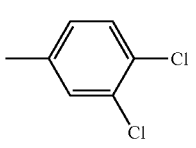 | CH₃CH₂ | H | 1 | 0 | CH | H | double bond (exocyclic) |
| V-30 | 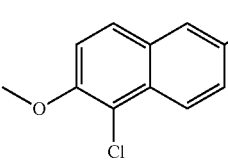 | 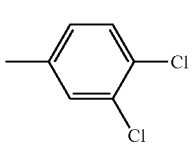 | CH₃CH₂ | H | 1 | 0 | CH | H | double bond (exocyclic) |
| V-31 | 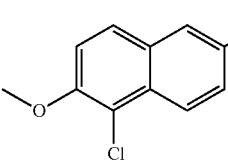 | Ph | H | H | 1 | 0 | CH | H | double bond (exocyclic) |
| V-32 | 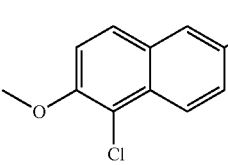 | Ph | H | H | 2 | 0 | CH | H | double bond (exocyclic) |
| V-33 | 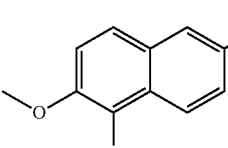 | 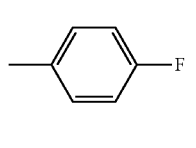 | CH₃ | H | 1 | 0 | CH | H | double bond (exocyclic) |
| V-34 | 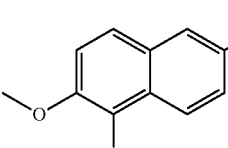 | 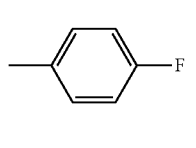 | CH₃ | H | 1 | 0 | CH | H | double bond (exocyclic) |

TABLE 1-continued

| No. | Ar₁ | Ar₂ | R₁ | R₂ | n | m | W | X | ----- |
|---|---|---|---|---|---|---|---|---|---|
| V-35 | 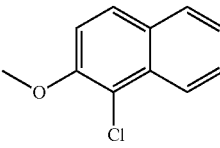 | 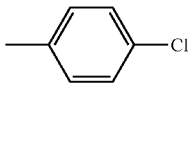 | CH₃ | H | 1 | 0 | CH | H | double bond (exocyclic) |
| V-36 | 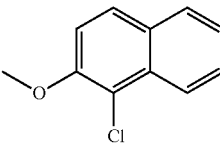 | 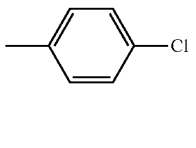 | CH₃ | H | 1 | 0 | CH | H | double bond (exocyclic) |
| V-37 | 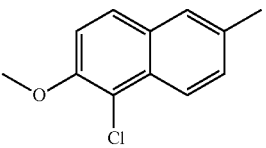 | Ph | CH₃ | H | 1 | 0 | CH | H | double bond (exocyclic) |
| V-38 | 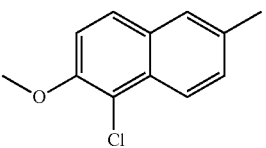 | Ph | CH₃ | H | 1 | 0 | CH | H | double bond (exocyclic) |
| V-39 | 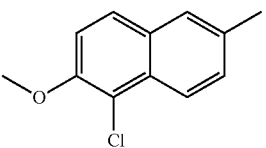 | Ph | CH₃ | H | 1 | 0 | CH₂ | H | double bond (endocyclic) |
| V-40 | 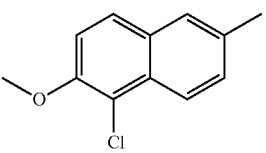 | Ph | CH₃ | H | 1 | 0 | CH₂ | H | double bond (endocyclic) |
| V-41 | 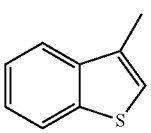 | Ph | CH₃ | H | 1 | 0 | CH₂ | H | double bond (endocyclic) |
| V-42 | 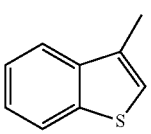 | Ph | CH₃ | H | 1 | 0 | CH₂ | H | double bond (endocyclic) |
| V-43 | 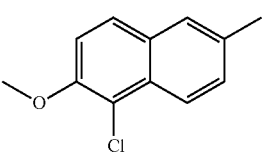 | Ph | CH₃CH₂ | H | 1 | 0 | CH₂ | H | double bond (endocyclic) |
| V-44 | 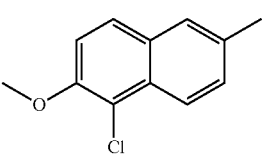 | Ph | CH₃CH₂ | H | 1 | 0 | CH₂ | H | double bond (endocyclic) |

TABLE 1-continued
| No. | Ar₁ | Ar₂ | R₁ | R₂ | n | m | W | X | ---- |
|---|---|---|---|---|---|---|---|---|---|
| V-45 | 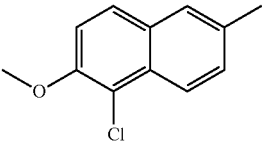 | Ph | H | H | 1 | 0 | CH₂ | H | double bond (endocyclic) |
| V-46 | 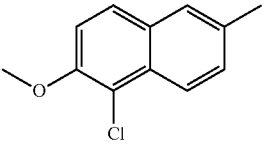 | Ph | H | H | 2 | 0 | CH₂ | H | double bond (endocyclic) |
| V-47 | 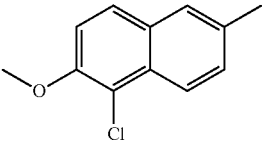 | 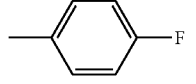 | CH₃ | H | 1 | 0 | CH₂ | H | double bond (endocyclic) |
| V-48 | 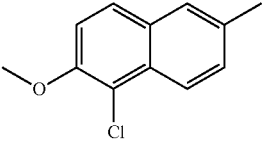 | 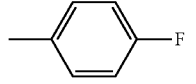 | CH₃ | H | 1 | 0 | CH₂ | H | double bond (endocyclic) |
| V-49 | 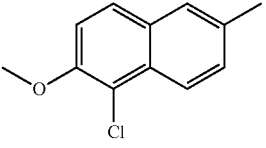 | Ph | CH₃ | H | 1 | 1 | O | H | single bond |
| V-50 | 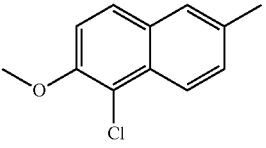 | Ph | CH₃ | H | 1 | 1 | O | H | single bond |
| V-51 | 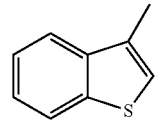 | Ph | CH₃ | H | 1 | 1 | O | H | single bond |
| V-52 | 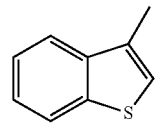 | Ph | CH₃ | H | 1 | 1 | O | H | single bond |
| V-53 | 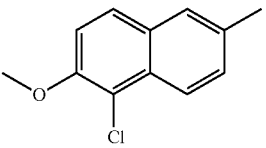 | Ph | CH₃CH₂ | H | 1 | 1 | O | H | single bond |
| V-54 | 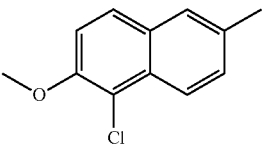 | Ph | CH₃CH₂ | H | 1 | 1 | O | H | single bond |

TABLE 1-continued

| No. | Ar₁ | Ar₂ | R₁ | R₂ | n | m | W | X | ---- |
|---|---|---|---|---|---|---|---|---|---|
| V-55 | 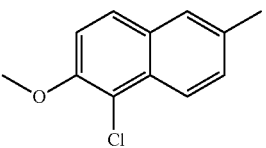 | Ph | H | H | 1 | 1 | O | H | single bond |
| V-56 | 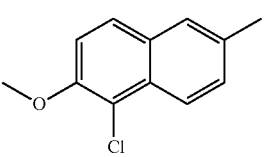 | Ph | H | H | 2 | 1 | O | H | single bond |
| V-57 | 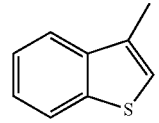 | Ph | H | H | 2 | 1 | O | H | single bond |
| V-58 | 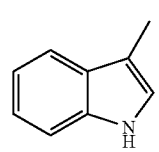 | Ph | H | H | 2 | 1 | O | H | single bond |
| V-59 | 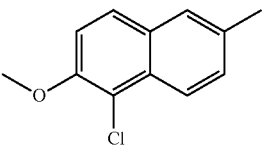 | 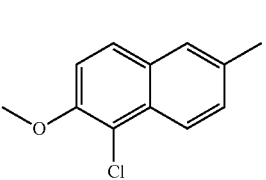 | CH₃ | H | 1 | 1 | O | H | single bond |
| V-60 | 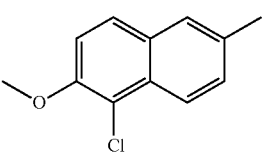 | 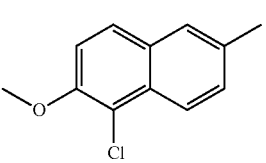 | CH₃ | H | 1 | 1 | O | H | single bond |
| V-61 | | | CH₃ | H | 1 | 1 | NH | H | single bond |
| V-62 | | | CH₃ | H | 1 | 1 | NH | H | single bond |
| V-63 | 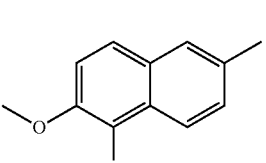 | Ph | H | H | 2 | 0 | CH₂ | OMe | single bond |

Compounds of the present invention are synthesized by the following methods:

Reacting halogenated aralkyl ketones (I) and substituted piperidines (II) in the presence of NEt₃ in DMF to obtain aralkyl ketone piperidines (III), the obtained aralkyl ketone piperidines (III) are reduced to aralkyl alcohol piperidines (IV) by NaBH₄ or aluminium isopropoxide, and compound (IV) is further subjected to column chromatography to obtain threo-form and erythro-form, respectively:

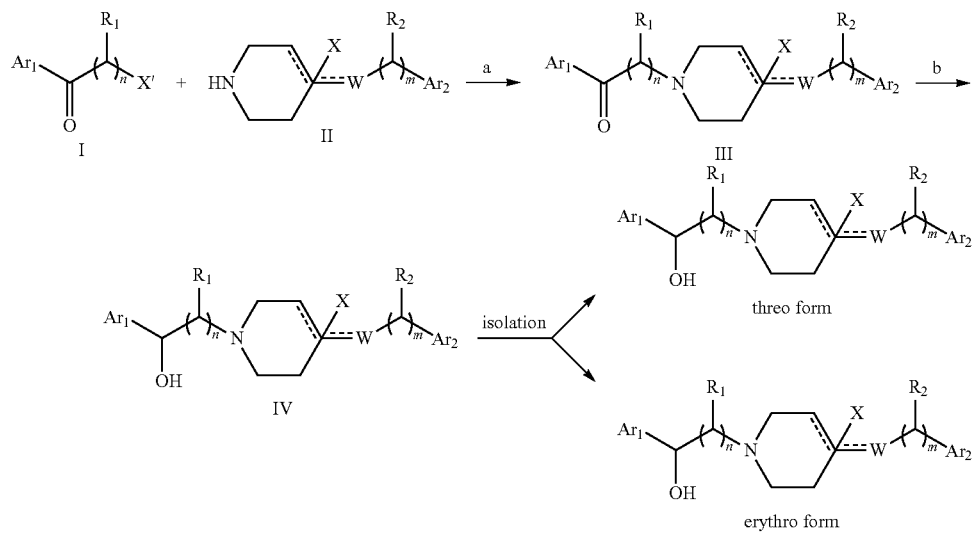

three form erythro form

The said threo or erythro is defined specifically in MARCH'S ADVANCED ORGANIC CHEMISTRY (the 6th edition P. 166).

$R_1$, $R_2$, $R_3$, $R_1$, $Ar_1$, $Ar_2$, W, X, Y, Z, n, m are the same as given above:

In the above procedure:

a: $NEt_3$, DMF b: $NaBH_4$, $CH_3OH$; or $AlCl_3$, Al (i-PrO—)$_3$, i-PrOH:

wherein:

The intermediate (I) is obtained through Friedel-Crafts acylation of the corresponding aromatic rings and then halogenation. The two-step synthesizing method is prepared by the method disclosed in Patent EP 284297.

The intermediate (II) is the key for the synthesis of the type of compounds, which is described below based on the specific structural type:

(1) The Intermediate (II) has 4-Hydroxypiperidine and 4-Methoxypiperidine Structures The key point of the synthesizing is the construction of piperidine position-4 hydroxyl, BOC-piperidine ketone is subjected to Grignard reaction with different halides, and then deprotection 1 to obtain the 4-hydroxypiperidine II (see the following general synthesis method one for details):

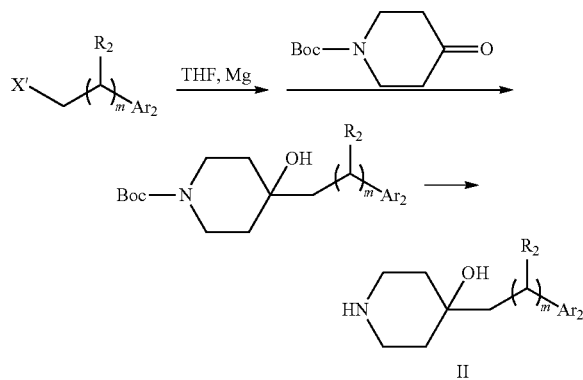

$R_2$, $Ar_2$, and m are the same as given above; X' is chlorine or bromine;

BOC-piperidine ketone can be commercially available, the said different halides can be prepared by the method disclosed in the document (Organic Syntheses 2006, 83, 38-44) or obtained commercially.

The 4-methoxypiperidines are obtained by subjecting the Boc protected 4-hydroxypiperidine compound to methylation of iodine methane and then de-Roe protection according to the method disclosed in the document (Journal of Medicinal Chemistry, 2007, 50 (4), 641-662):

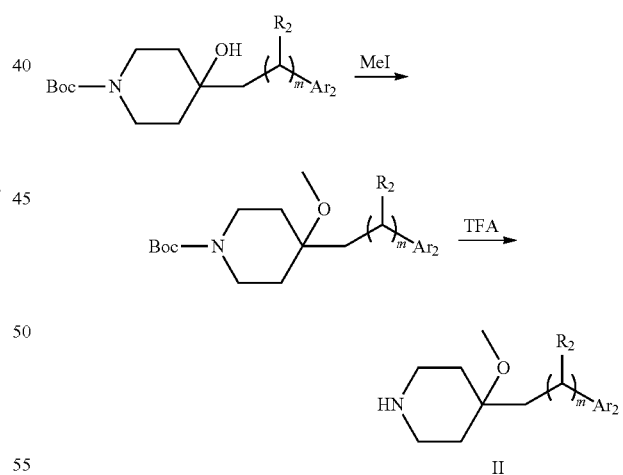

$R_2$, $Ar_2$, and m are the same as given above, X' is chlorine or bromine:

(2) The Intermediate (II) has 1,2,3,6-Tetrahydropyridine Structure

Reducing 4-aryl pyridines in $AlCl_3$ and $LiAlH_4$ in diethyl ether to obtain 4-aryl-1,2,3,6-tetrahydropyridines (see the synthesis method two for details):

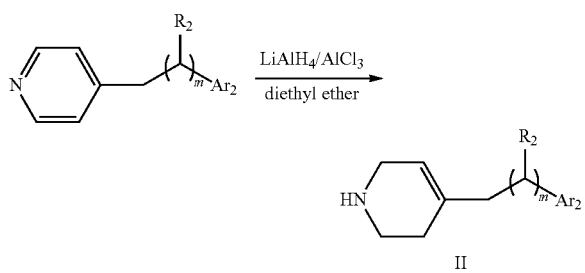

$R_2$, $Ar_2$, and m are the same given as above;

(3) The Intermediate II has Piperidine-Alkylidene Structure

First of all, the corresponding halides and triphenylphosphine are used to form Ylide salt, the Ylide salt is subjected to Witting reaction with the protected piperidine ketones in the presence of butyl lithium, the produced protected product is subjected to deprotection to obtain the key intermediate piperidine-alkylidene (II), (see the synthesis method three for details):

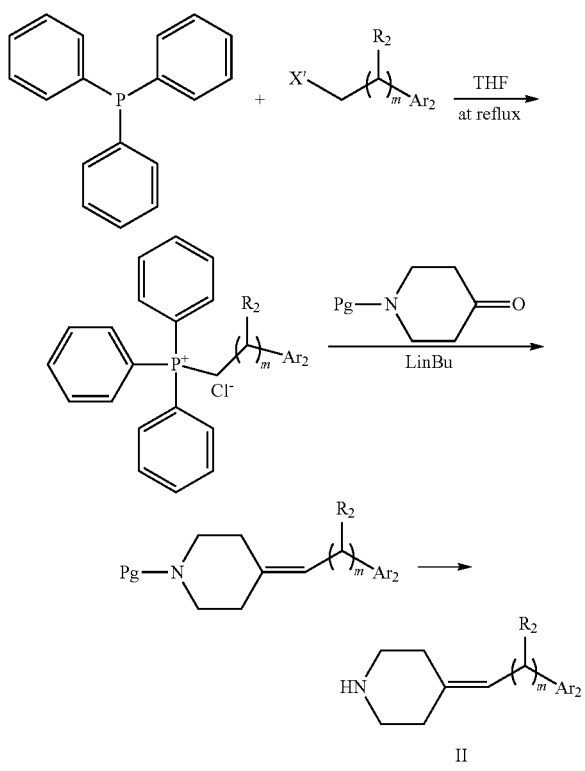

The corresponding halides refer to chlorides or bromides, which can be prepared by the method disclosed in the document (Organic Syntheses 2006, 83, 38-44), or commercially available products can be used. The protected piperidine ketones such as BOC-piperidine ketone or benzyl can be commercially available. $R_2$, $Ar_2$, and m are the same given as above, X' is chlorine or bromine:

(4) The Intermediate (II) has a 4-Ether Piperidine Structure

First of all, the Roc protected piperidine alcohol is reacted with halides under the activity of sodium hydride, the obtained Roc protected ether is subjected to TFA deprotection to obtain 4-ether piperidines (II) (see the synthesis method four for details):

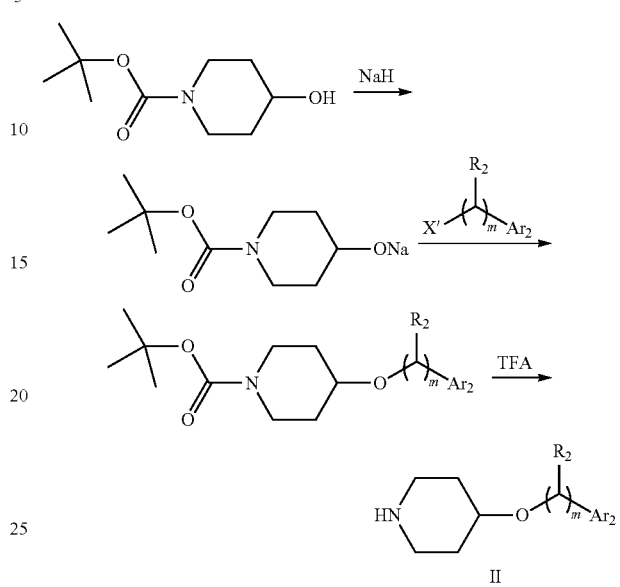

The Boc protected piperidine alcohol is market available.

$R_2$, $Ar_2$, and m are the same given as above, X' is chlorine or bromine:

(5) The Intermediate (II) has a 4-Aminopiperidine Structure

First of all, the Roe protected piperidine ketone and amine are subjected to reduction amination to obtain intermediate 2 with the catalyzation of palladium on carbon, the intermediate 2, TsCl, and pyridine are reacted in $CH_2Cl_2$ to produce protected intermediate 3, the intermediate 3 is subjected to TFA deprotection to obtain 4-aminopiperidines (II), (see the synthesis method live for details):

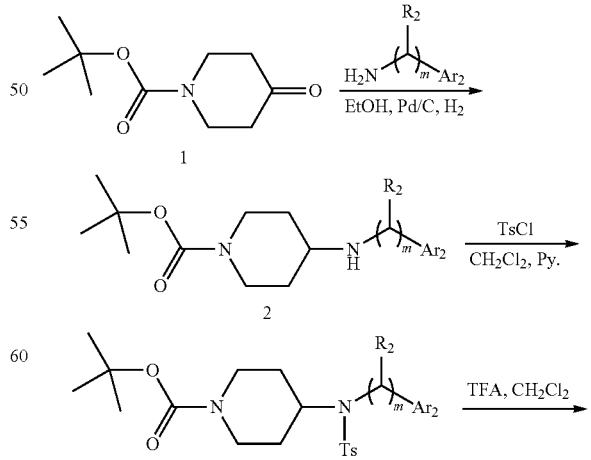

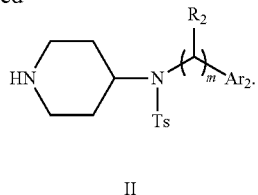

II

The said aminated compound can be prepared with the method disclosed in the document (Tetrahedron Letters, 2004, 45 (2), 397-399):

$R_2$, $Ar_2$, and m are the same as given above;

The intermediate (II) is subjected to condensation with halogenated aroylalkyl compound (I), reduction with aluminium isopropoxide or sodium borohydride, and then silica gel column chromatography to obtain aralkyl alcohol piperidine compound.

The present invention relates to the said aralkyl alcohol piperidine derivative, which has triple inhibition activity on the reuptake of 5-HT, NA and DA, and can be used in the manufacture of antidepressants.

The derivative of the present invention can be administered to the patient in need of such treatment in form of a composition through oral administration or injection.

Said composition comprises a therapeutically effective amount of the above compound or a free base or a salt thereof and a pharmaceutically acceptable carrier.

The said carrier is a conventional carrier in the pharmaceutical field, such as: diluents, excipients such as water, etc.; adhesives such as cellulose derivatives, gelatin, polyvinylpyrrolidone, etc.; fillers such as starch, etc; disintegrating agents such as calcium carbonate, sodium bicarbonate; in addition, the composition can be further added with other adjunct agents such as flavors and sweeteners.

When for oral administration, the composition can be formulated to conventional solid formulations such as tablets, powders or capsules: when for injection, it can be prepared as an injection.

The composition of the present invention can be formulated to various formulations through conventional methods in the pharmaceutical field, wherein the content of the active ingredient is from 0.1% to about 99.5% by weight.

The dosing amount of the present invention varies depending on the administration manners, age and weight of a patient, and the type and conditions of diseases to be treated. The daily dosage is from 5-30 mg/kg weight (for an oral administration) or 1-10 mg/kg weight (for an injection).

The composition or a free base or a salt thereof of the present invention exhibits antagonistic activity to a depression in animal tests.

The inventor of the present invention finds that the anti-depression activity of the derivatives of the present invention is useful in more indicators, has less side-effect and lower toxicity, and less side effect on nervous system as compared with the current clinically used antidepressant having a single mechanism such as Desipramine or Fluoxetine as well as the current clinically used antidepressant having a dual mechanism such as Venlafaxine.

MODE OF CARRYING OUT THE INVENTION

General Synthesis Method One

A: preparation of 4-aryl(alkyl)-4-hydroxypiperidine

Magnesium powder (44 mmol) is added to 5 mL of anhydrous THF (5 mL), thereto a solution of aryl(alkyl)halide (40 mmol) in anhydrous THF (30 mL) is added, and a small pellet of iodine is added to initiate reaction while controlling the temperature <−5° C. Continue drop-adding the remaining solution of aryl(alkyl)halide. Stirring reaction for one hour after completion of addition. Drop-adding THF (20 mL) solution of 4-piperidine ketone (40 mmol), then the reaction is allowed to warm to room temperature after completion of addition, and stirred for three hours. TLC shows (ethyl acetate:petroleum ether=3:1) completion of reaction, adding 20 mL of a saturated $NH_4Cl$ solution for quenching, and most of the THF is evaporated from the reaction solution. The residue is added by water (20 mL) and extracted with ethyl acetate (30 mL×3). The organic phase is combined, washed with saturated NaCl (10 mL×3), evaporated off solvent, and subjected to silica gel column chromatography (ethyl acetate: petroleum ether=50:1 to about 20:1) to obtain a product as a light yellow oil with yield of 75-85%. The product as a light yellow oil is dissolved in $CH_2Cl_2$, 15 mL), thereto TFA (0.5 mL) is drop-added. After stirring at room temperature for lour hours after completion of addition, the solvent is evaporated off to obtain a light yellow solid with yield of 90-95%.

B: the preparation of 4-aryl(alkyl)-4-methoxypiperidine

To obtain Boc protected 4-hydroxypiperidines according to the reaction in A. The Boc protected 4-hydroxypiperidine compound (10 mmol) is dissolved in THF (30 mL), thereto sodium hydride (20 mmol) with 55% content is added, and then heated to 50° C. to react for two hours. Then adding MeI (4 mL), and refluxing the reaction for 12 hours. After cooled to 0° C., the reaction is diluted with saturated $NaHSO_4$ aqueous solution (10 mL) and separated. The aqueous layer is extracted two times with diethyl ether (2×10 mL). The organic layer is combined, dried over anhydrous $MgSO_4$, filtered and concentrated, and subjected to silica gel column chromatograph (eluent: ethyl acetate/petroleum ether 1/10), to obtain the product as a white solid, with yield of 50%. The Boc-protected product is dissolved in $CH_2Cl_2$, 15 mL), thereto TFA (0.5 mL) is drop-added, and stirred at room temperature for four hours after completion of addition. The solvent is evaporated off to obtain a white solid, with yield of 90%.

Synthesis method two: preparation of 4-aryl(alkyl)-1,2,3,6-tetrahydropyridine salt $LiAl_4$ (95 mmol) is added to anhydrous diethyl ether (130 mL), meanwhile the temperature is controlled <5° C., then thereto an anhydrous diethyl ether (50 mL) solution of $AlCl_3$ (33 mmol) is added. After completion of addition, the reaction is allowed to warm to room temperature, and stirred for one hour. The temperature is controlled at 0° C., meanwhile an anhydrous diethyl ether (50 mL) solution of 4-aryl(alkyl) pyridine (60 mmol) is drop-added. After completion of addition, the reaction is slowly heated to reflux after completion of addition and allowed to react for eight hours. The temperature is decreased to below 15° C., and then the reaction is quenched with drop-addition of 100 mL of 10% HCl aqueous solution. After separation, the ether layer is extracted with 10% HCl aqueous solution (20 mL×2) and combined with all aqueous layers. The combined aqueous layer is neutralized to be basic with $NH_4OH$ solution having a weight concentration of 25%, and extracted with ethyl acetate (25 mL×3). The organic layers are combined and dried over anhydrous $Na_2SO_4$. After filtration, the filter residue is washed with small amount of acetate ethyl. The filtrate is concentrated to ⅓ of the volume. The concentrated filtrate is made acidic by drop-adding 2 mol/L of EtOH—HCl, and a white solid is precipitated. After filtration, the filter cake is washed with small amount of ethanol and dried at room temperature in vacuum, to obtain a product as a white solid, with yield of 50-60%.

Synthesis method three: preparation of 4-aryl(alkyl)methylenepiperidine hydrochloride Benzyl aryl(alkyl)halide (0.1 mol), triphenylphosphine (0.1 mol) are dissolved in anhydrous THF (100 mL) and heated to reflux. A solid is precipitated eventually, and the reaction is continued for 24 hours. The reaction solution is cooled to room temperature, filtered, and the filter cake is washed with small amount of THF, to obtain aryl(alkyl)halide triphenyl phosphonium chloride as a white solid, with yield of 5-89%, and stored in a desiccator.

The reaction bottle is homing dried and purged with nitrogen gas, and a passage of nitrogen gas through the bottle is continued for protection. Dispersing acry(alkyl)halide triphenyl phosphonium chloride (10 mmol) in TIE (45 mL), The temperature is controlled at <5° C. meanwhile slowly adding n-butyl lithium (2.5 mol/L n-hexane solution, 4 mL) with injector, naturally elevating temperature and stirring reaction for two hours to obtain benzyl phosphine ylide. The reaction solution has a color of clear yellow. Adding N—BOC piperidine ketone (10 mmol), and stirring reaction for 12 hours at r.t. To the reaction solution is added 70 mL n-hexane and a sticky yellow semi-solid is precipitated. The semi-solid is stirred with glass rod, solidifies eventually and is dispersed to form a light yellow solid, which is triphenylphosphine oxide. After filtration, the filtrate is evaporated to remove the solvent, to obtain a product as a light yellow oil. Adding 3 mL of trifluoroacetic acid, the temperature is controlled at 55° C., and reacting for two hours, thereafter TLC ($CH_2Cl_2$:MeOH=20:1) shows disappearance of spots of the raw materials. Most of the trifluoroacetic acid is evaporated out of the reaction solution in vacuum, and eluting with saturated $Na_2CO_3$/ethyl acetate. The organic phase is dried over anhydrous $Mg_4SO_4$ and filtered, and the filter residue is washed with small amount of ethyl acetate. The filtrate is made acidic with 2 mol/L of HCl/ether to pH of about 3. After filtration, a crystal as a white flake is obtained, with yield of 76-80%.

Synthesis method four: synthesis of 4-aryl(alkyl)oxy piperidine 4-hydroxy-N-BOCpiperidine (10 mmol) is dissolved in THF (20 mL), thereto 55 wt % sodium hydride (13 mmol) is added, meanwhile stirring the reaction at reflux 30 min. After cooling to r.t., aryl(alkyl)halide (12 mmol) is added, then the temperature is elevated to 50° C., and meanwhile stirring reaction for eight hours. TLC (ethyl acetate:petroleum ether=1:5) shows that the reaction is completed. After cooling to r.t., water (20 mL) is added carefully to quench the reaction. The reaction solution is extracted with ethyl acetate/water (50 mL/20 mL), and the organic phase is dried over $Mg_2SO_4$. After filtration, the filter residue is washed with small amount of ethyl acetate. The filtrate is evaporated to remove the solvent to obtain a product as a light yellow oil. Adding trifluoroacetic acid (5 mL) to the oily product, and stirring reaction at temperature of 35-40° C. for 30 min. TLC (ethyl acetate:petroleum ether=1:5) shows that the reaction is completed. Most of the trifluoroacetic acid is evaporate out in vacuum and saturated $Na_2CO_3$ is added for neutralizing to pH=9-10. After extracting with ethyl acetate/water (30 mL/20 mL), the organic phase is washed with saturated NaCl (30 mL×3) and dried over anhydrous $Na_2SO_4$ overnight. After filtration out the dessicant, the solvent is evaporated out of the filtrate in vacuum, and the obtained product as a light yellow oil solidified gradually after standing with yield of 75-80%.

Synthesis method five: synthesizing 4-aryl(alkyl)amino piperidine

10% of Pd/C (10% wt) is dissolved in EtOH (10 mL), adding 1-BOC-4-piperidine ketone (10 mmol) and aryl(alkyl) amine (12 mmol) dissolved in EtOH (20 mL) under protection of nitrogen gas. After completion of addition, hydrogenation is carried out under 60 psi for one hour. The catalyst is removed by filtration. The filtrate is concentrated in vacuum to obtain a colorless secondary amine (yield of 90-98%). The said secondary amine (8 mmol) is dissolved in $CH_2Cl_2$ (10 mL) and thereto pyridine (16 mmol) is added, meanwhile a temperature is maintained at below 10° C. Drop-adding $CH_2Cl_2$ solution of 4-methylphenylsulfurylchloride (9.6 mmol) with stirring, elevating temperature to 30° C., after completion of addition, and stirring reaction for four hours. The organic phase is extracted with water (10 mL) and dried over $Mg_2SO_4$. After filtration, the filtrate is evaporated to remove most of the solvent. After addition of trifluoroacetic acid (5 mL), the reaction is stirred at 35° C. for 30 min, and most of the trifluoroacetic acid is evaporated out in vacuum. Saturated $Na_2CO_3$ is added for neutralizing to pH=9-10 and extracted with $CH_2Cl_2$/water (30 mL/10 mL). The organic phase is washed with saturated NaCl (30 mL×3) and dried over anhydrous $Mg_2SO_4$ overnight. After filtering out of the dessicant, the filtrate is concentrated in vacuum to evaporate out solvent, to obtain a light yellow solid with yield of 85-92%.

Synthesis method six: synthesis of 4-aryl(alkyl)-N-aralkyl acylalkyl piperidine hydrochloride 4-aryl(alkyl) piperidine (20 mmol), halogenated acyl-5-chloro-6-methoxynaphthalene (20 mmol), triethylamine (60 mmol) are mixed in DMF (100 mL), and the reaction is stirred at room temperature for 10 hours. When TLC (ethyl acetate:petroleum ether=1:5) shows that the reaction is completed, the reaction solution is poured into 400 mL of water and extracted with ethyl acetate. The organic phase is washed with water (20 mL×3) and saturated NaCl (20 mL×2) to be made neutral, and dried over anhydrous $NaSO_4$ overnight. After filtering out the dessicant, the filter residue is washed with small amount of ethyl acetate. The filtrate is evaporated to remove most of the solvent, and thereto 4 mol/L EtOH—HCl is drop-added to make pH of about 3. After filtration, the filter cake is washed with small amount of ethanol/ethyl acetate (1:1) and dried in vacuum, to obtain 4-aryl(alkyl)-N-aralkylacylalkylpiperidine hydrochloride as a solid with yield of 70-85%.

Synthesis method seven: synthesis of 4-aryl(alkyl)-N-aralkyl alcohol piperidine hydrochloride Method A: 4-aryl(alkyl)-N-aralkylacylalkylpiperidine hydrochloride (10 mmol) is eluted with saturated $NaCO_3$ solution/ethyl acetate (50 mL/50 mL). The organic phase is washed with saturated NaCl to be made neutral, and dried over anhydrous $MgSO_4$. The dessicant is filtered out, and the filter residue is washed with small amount of ethyl acetate.

The filtrate is evaporated to remove the solvent to obtain the product as a oil, free 4-aryl(alkyl)-N-aralkylacylalkylpiperidine.

Aluminium isopropoxide (3.6 g, 17.5 mmol) is dispersed in isopropyl alcohol (40 mL), thereto anhydrous $AlCl_3$ (0.25 g, 3.3 mmol) is added. The temperature is controlled at 50° C. with stirring for three hours until the solution is clear. To the solution the above free 4-aryl(alkyl)-N-aralkylacylalkylpiperidine is added, and the reaction is stirred while controlling a temperature at 60-65° C. until TLC ($CH_2Cl_2$:MeOH=15:1) shows disappear of spots of the raw materials. The reaction solution is adjusted with 15% of NaOH to pH of about 7 and extracted with methylene chloride or ethyl acetate. The organic phase is washed with saturated NaCl (20 mL×3) and dried over anhydrous $MgSO_4$. After filtering out the dessicant, the filter residue is washed with small amount of ethyl acetate, and the filtrate is evaporated to remove the solvent. The obtained residue is subjected to silica gel column chromatography separation ($CH_2Cl_2$:MeOH=300:1 to about 75:1) to form a hydrochloride, then a hydrochloride of threo and a hydrochloride of erythro products are obtained, respectively. The total yield of both is 60-75%.

Method B: 4-aryl(alkyl)-N-aralkylacylalkylpiperidine hydrochloride (10 mmol) is dispersed or dissolved in methanol (10 mL) while controlling a temperature <10° C., thereto $NaBH_4$ (5 mmol) is added portion-wise and the reaction is stirred. After TLC ($CH_2Cl_2$:MeOH=15:1) shows disappearance of spots of the raw materials, 5% of HCl is added to make pH=4 to destroy unreacted $NaBH_4$. The reaction solution is evaporated to remove methanol, thereto methanol (20 mL) is added. The mixture is evaporated to dryness, which is repeated for three times to destroy possibly existed boron complex. The residue is subjected to elution with saturated $Na_2CO_3$/ethyl acetate (30 mL:30 mL). The organic phase is washed with saturated NaCl (20 mL×2) and dried over anhydrous $MgSO_4$. After filtering out the dessicant, the filter residue is washed with small amount of ethyl acetate, and the filtrate is evaporated to remove the solvent, then the obtained residue is subjected to silica gel column chromatography separation ($CH_2Cl_2$:MeOH=300:1 to about 75:1), to form a hydrochloride, then a hydrochloride threo and a hydrochloride of erythro products are obtained, respectively, the total yield of both is 50-60%.

If the product does not have isomerization of configuration, 2 mol/L of EtOH—HCl is drop-added to make of about 4. The solid is precipitated and filtered, then the filter residue is washed with small amount of ethanol, and the filtrate is evaporated to remove the solvent. The obtained residue is subjected to silica gel column chromatography separation ($CH_2Cl_2$:MeOH=300:1 to about 75:1), after formation of a hydrochloride, a hydrochloride of 4-aryl(alkyl)-N-aralkyl alcohol piperidine is obtained with yield of 85-90%.

Example 1

A hydrochloride of V-1 (Threo-) and of V-2 (Erythro-) 4-benzyl-N-[1-methyl-2-hydroxy-2-(5-chloro-6-methoxynaphthalene-2-yl)]ethylpiperidine 2-bromo-1-(5-chloro-6-methoxynaphthaleneyl-2-yl)-acetone (10 mmol), 4-benzylpiperidine (8 mmol), and triethylamine (30 mmol) are dissolved in DMF (50 mL) and operated according to the general synthesis method six to obtain 3.50 g of a white solid with yield of 92.1% (calculated based on 4-benzylpiperidine). MS (m/z): 422.1 $[M+1]^+$.

The product is further reduced with $NaBH_4$ according to the general synthesis method seven and subjected to silica gel column chromatography separation ($CH_2Cl_2$:MeOH=300:1~75:1). After formation of a hydrochloride, a hydrochloride of threo form V-1 (0.70 g, with yield of 25%) and a hydrochloride of erythro form V-2 (1.12 g, with yield of 40.5%) are obtained, respectively.

V-1: m.p=254.4-255.7° C. (decomposition). MS (m/z): 424.1 $[M+1]^+$. $^1$HNMR ($CDCl_3$): 8.18 (d, J=8.8 Hz, 1H, Ar—H), 7.73 (d, J=11.6 Hz, 2H, Ar—H), 7.56 (dd, J=8.8, 1.6 Hz, 1H, Ar—H), 7.24-7.30 (m, 3H, Ar—H), 7.14-21 (m, 3H, Ar—H), 5.15 (br, 1H, disappears upon addition of $D_2O$, >CH—OH), 4.37 (d, J=9.6 Hz, 1H, >CH—OH), 4.01 (s, 3H, —O—$CH_3$), 2.86-2.89 (m, 1H, —CH$CH_3$), 2.62-2.71 (m, 2H, —N—$CH_2$—), 2.51-2.58 (m, 2H, CH—$CH_2$-Ph), 1.72-1.75 (m, 2H, —N—$CH_2$—), 1.54-1.59 (m, 1H, CH—$CH_2$-Ph), 1.28-1.45 (m, 4H, —$(CH_2)_2$—CH—), 0.75 (d, J=6.8 Hz, 3H, >CH—$CH_3$).

V-2: m.p=256.4-258.1° C. (decomposition). MS (m/z): 424.1 $[M+1]^+$. $^1$HNMR ($CDCl_3$): 8.15 (d, J=8.8 Hz, 1H, Ar—H), 7.73-7.76 (m, 2H, Ar—H), 7.46 (dd, J=8.8, 1.2 Hz, 1H, Ar—H), 7.25-7.29 (m, 3H, Ar—H), 7.13-7.19 (m, 3H, Ar—H), 4.98 (d, J=4.0 Hz, 1H, >CH—OH), 4.01 (s, 3H, —O—$CH_3$), 3.09-3.11 (m, 1H, —CH—$CH_3$), 2.76-2.82 (m, 2H, —N—$CH_2$—), 2.55 (d, J=6.8 Hz, 2H, CH—$CH_2$-Ph), 2.03-2.31 (m, 2H, —N—$CH_2$—), 1.60-2.03 (m, 2H, —$CH_2$—CH—), 1.52-1.57 (m, 1H, CH—$CH_2$-Ph), 1.25-1.35 (m, 2H, —$CH_2$—CH—), 0.83 (d, J=6.8 Hz, 3H, >CH—$CH_3$).

Example 2

A hydrochloride of V-3 (Threo-) and of V-4 (Erythro-) 4-benzyl-N-[1-methyl-2-hydroxy-2-(benzothiophene-3-yl)]ethylpiperidine 2-bromo-1-(benzothiophene-3-yl)-acetone (10 mmol), 4-benzylpiperidine (8 mmol), and triethylamine (30 mmol) are dissolved in DMF (50 mL) and operated according to the general synthesis method six to obtain 2.3 g of a white solid, with yield of 89.7% (calculate based on 4-benzylpiperidine). MS (m/z): 364.1 $[M+1]^+$.

The product is further reduced with $NaBH_4$ according to the general synthesis method seven and subjected to silica gel column chromatography separation ($CH_2Cl_2$:MeOH=300:1 to about 100:1). After formation of a hydrochloride, a hydrochloride of threo form V-3 (0.50 g, yield of 20.5%) and a hydrochloride of erythro form V-4 (0.80 g, yield of 31.6%) are obtained, respectively.

V-3: MS (m/z): 366.2 $[M+1]^+$. $^1$HNMR ($CDCl_3$): —(dd, 2H, Ar—H), 7.12-7.22 (m, 7H, Ar—H), 6.85 (s, 1H, Ar—H), 5.10 (br, 1H, disappears upon addition of $D_2O$, >CH—OH), 4.48 (d, J=9.7 Hz, 1H, >CH—OH), 4.03 (s, 3H, —O—$CH_3$), 2.88-2.91 (m, 1H, —CH$CH_3$), 2.62-2.71 (m, 2H, —N—$CH_2$—), 2.51-2.58 (m, 2H, CH—$CH_2$-Ph), 1.70-1.75 (m, 2H, —N—$CH_2$—), 1.55-1.61 (m, 1H, CH—$CH_2$-Ph), 1.28-1.45 (m, 4H, —$(CH_2)_2$—CH—), 0.75 (d, J=6.8 Hz, 3H, >CH—$CH_3$).

V-4: MS (m/z): 366.2 $[M+1]^+$. $^1$HNMR ($CDCl_3$): —(dd, 2H, Ar—H), 7.14-7.29 (m, 7H, Ar—H), 6.87 (s, 1H, Ar—H), 5.12 (br, 1H, disappears upon addition of $D_2O$, >CH—OH), 4.88 (d, J=4.0 Hz, 1H, >CH—OH), 4.00 (s, 3H, —O—$CH_3$), 3.07-3.11 (m, 1H, —CH$CH_3$), 2.76-2.82 (m, 2H, —N—$CH_2$—), 2.55 (d, J=6.8 Hz, 2H, CH—$CH_2$-Ph), 2.03-2.31 (m, 2H, —N—$CH_2$—), 1.60-2.03 (m, 2H, —$CH_2$—CH—), 1.52-1.57 (m, 1H, CH—$CH_2$-Ph), 1.25-1.35 (m, 2H, —$CH_2$—CH—), 0.83 (d, J=6.8 Hz, 3H, >CH—$CH_3$).

Example 3

A hydrochloride of V-5 (Threo-) and of V-6 (Erythro-) 4-benzyl-N-[1-ethyl-2-hydroxy-2-(5-chloro-6-methoxynaphthalene-2-yl)]ethylpiperidin 2-bromo-1-(5-chloro-6-methoxynaphthaleneyl-2-yl)-butanone (10 mmol), 4-benzylpiperidine (8 mmol), and triethylamine (30 mmol) are dissolved in DMF (50 mL) and operated according to the general synthesis method six to obtain 3.45 g of a white solid with yield of 91.3% (calculated based on 4-benzylpiperidine), m.p=237.6-239.0° C. MS (m/z): 422.1 [M+1]$^+$.

The product is further reduced with aluminium isopropoxide according to the general synthesis method seven, and subjected to silica gel column chromatography separation ($CH_2Cl_2$:MeOH=300:1 to about 75:1). After formation of a hydrochloride, a hydrochloride of threo form V-5 (0.73 g, yield of 25.2%) and a hydrochloride of erythro form V-6 (1.20 g, yield of 41.0%) are obtained, respectively.

V-5: m.p=254.6-255.9° C. (decomposition). MS (m/z): 439.1 [M+1]$^+$. $^1$HNMR ($CDCl_3$): 8.15 (d, J=8.8 Hz, 1H, Ar—H), 7.70 (d, J=11.6 Hz, 1H, Ar—H), 7.55 (dd, J=8.8, 1.6 Hz, 1H, Ar—H), 7.23-7.32 (m, 3H, Ar—H), 7.15-21 (m, 3H, Ar—H), 5.14 (br, 1H, disappears upon addition of $D_2O$, >CH—OH), 4.37 (d, J=9.6 Hz, 1H, >CH—OH), 4.02 (s, 3H, —O—$CH_3$), 2.86-2.89 (t, 1H, —CH$CH_2$CH$_3$), 2.62-2.71 (m, 2H, —N—$CH_2$—), 2.51-2.58 (m, 2H, CH—$CH_2$-Ph), 1.72-1.74 (m, 2H, —N—$CH_2$—) 1.54-1.59 (m, 1H, CH—$CH_2$-Ph), 1.26-1.45 (m, 4H, —($CH_3$)$_2$—CH—), 1.23-1.50 (m, 2H, —CH$CH_2$CH$_3$), 0.75 (d, J=6.8 Hz, 3H, >CH$CH_2$$CH_3$).

V-6: m.p=256.7-258.0° C. (decomposition). MS (m/z): 439.1 [M+1]$^+$. $^1$HNMR ($CDCl_3$): 8.16 (d, J=8.8 Hz, 1H, Ar—H), 7.73-7.76 (m, 2H, Ar—H), 7.46 (dd, J=8.8, 1.2 Hz, 1H, Ar—H), 7.25-7.28 (m, 3H, Ar—H), 7.14-7.19 (m, 3H, Ar—H), 4.95 (d, J=4.0 Hz, 1H, >CH—OH), 4.00 (s, 3H, —O—$CH_3$), 3.09-3.11 (t, 1H, —CH$CH_2$CH$_3$), 2.76-2.82 (m, 2H, —N—$CH_2$—), 2.55 (d, J=6.8 Hz, 2H, CH—$CH_2$-Ph), 2.03-2.33, (m, 2H, —N—$CH_2$—), 1.60-2.03 (m, 1.52-1.57 (m, 1H, CH—$CH_2$-Ph), 1.25-1.35 (m, 2H, —$CH_2$—CH—), 1.25-1.55 (m, 2H, —CH$CH_2$CH$_3$), 0.83 (d, J=6.8 Hz, 3H, >CH$CH_2$$CH_3$).

Example 4

A hydrochloride of V-7 4-benzyl-N-[2-hydroxy-2-(5-chloro-6-methoxynaphthalene-2-yl)]ethylpiperidine 2-bromo-1-(5-chloro-6-methoxynaphthalene-2-yl)-ethanone (10 mmol), 4-benzylpiperidine (8 mmol), and triethylamine (30 mmol) are dissolved in DMF (50 mL) and operated according to the general synthesis method six to obtain 3.42 g of a white solid with yield of 96.3% (calculated based on 4-benzylpiperidine). MS (m/z): 410.0 [M+1]$^+$.

The product is further reduced with $NaBH_4$ according to the general synthesis method seven, and subjected to silica gel column chromatography separation ($CH_2Cl_2$:MeOH=300:1~75:1). After formation of a hydrochloride, a hydrochloride of V-7 (2.40 g, yield of 71%) is obtained. m.p=248.4-250.5° C.

Element analysis: $C_{25}H_{28}ClNO_2$·HCl (calculated value %: C, 67.26; H, 6.55; N, 3.14. found value %: C, 67.15; H, 6.547; N, 3.12).

MS: m/z 410.2 [M+1]$^+$.

Example 5

A hydrochloride of V-8 4-benzyl-N-[2-hydroxy-2-(benzothiophene-3-yl)]ethylpiperidine Chloroacetyl chloride (28.4 mmol) is dissolved in chloroform (30 ml), thereto $AlCl_3$ (30.8 mmol) is added, and the mixture is stirred one hour at room temperature. $AlCl_3$ slowly dissolved, and the color of the solution is darkened to light brown. Temperature is controlled at <10° C., meanwhile slowly drop-adding chloroform (10 ml) solution of benzothiophene (23.7 mmol). After completion of drop-addition, the reaction is allowed to warm to room temperature and stirred for one hour, thereafter the color of the reaction solution is darkened to be brown. The reaction solution is poured to a mixture of hydrochloric acid (20 ml)/crashed ice (50 g) with stirring, and the color of the organic phase is faded to light yellow to yellow. Separating the organic phase, and the aqueous phase is washed with water (20 ml×3) until neutral and dried over anhydrous $Na_2SO_4$ overnight. After filtering out dessicants, the filter residue is washed with small amount of chloroform. The filtrate is evaporated to remove the solvent to obtain the product as a light yellow oil. Column chromatography to separate the product (ethyl acetate:petroleum ether=1:400 to about 1:60) as a light yellow oil, the product solidified after standing with yield of 58%.

2-Chloroacetyl-3-benzothiophene (10 mmol), 4-benzylpiperidine (8 mmol), and triethylamine (30 mmol) are dissolved in DMF (50 mL) and operated according to the general synthesis method six to obtain 2.43 g of a white solid with yield of 90.0% (calculated based on 4-benzylpiperidine). MS (m/z): 350.1 [M+1]$^+$.

The product is further reduced with $NaBH_4$ according to the general synthesis method seven, and subjected to silica gel column chromatography separation ($CH_2Cl_2$:MeOH=300:1 to about 150:1). After formation of a hydrochloride, a hydrochloride of V-8 (1.50 g, with yield of 61.4%) is obtained.

Element analysis: $C_{22}H_6ClNOS$ (calculated value %: C, 68.11; H, 6.75; N, 3.61; S, 8.26. found value %: C, 68.15; H, 6.76; N, 3.62; S, 8.24).

MS: m/z 352.0 [M+1]$^+$.

Example 6

A hydrochloride of V-9 4-benzyl-N-[3-hydroxy-3-(5-chloro-6-methoxynaphthalene-2-yl)]propylpiperidine 3-chloro-1-(5-chloro-6-methoxynaphthalene-2-yl)-acetone (10 mmol), 4-benzylpiperidine (8 mmol), and triethylamine (30 mmol) are dissolved in DMF (50 mL), and operated according to the general synthesis method six to obtain 3.48 g of a white solid with yield of 91.1% (calculated based on 4-benzylpiperidine). MS (m/z): 422.0 [M+1]$^+$.

The product is further reduced with $NaBH_4$ according to the general synthesis method seven, and subjected to silica gel column chromatography separation ($CH_2Cl_2$:MeOH=300:1 to about 75:1). After formation of a hydrochloride, a hydrochloride of V-9 (2.60 g, with yield of 74.4%) is obtained.

Element analysis: $C_{26}H_{30}ClNO_2$·HCl (calculated value %: C, 67.82; H, 6.79; N, 3.04. found value %: C, 67.75; H, 6.80; N, 3.02).

MS: m/z 424.2 [M+1]$^+$.

Example 7

A hydrochloride of V-10 4-benzyl-N-[3-hydroxy-3-(benzothiophene-3-yl)]propylpiperidine 3-bromopropionyl chloride (28.4 mmol) is dissolved in chloroform (30 ml), thereto $AlCl_3$ (30.8 mmol) is added, and the mixture is stirred one hour at room temperature. $AlCl_3$ dissolves eventually, and the color of solution is darkened to light brown. Temperature is controlled at <10° C., meanwhile slowly drop-adding chloroform (10 ml) solution of benzothiophene (23.7 mmol), and then the reaction is allowed to warm to room temperature. After completion of addition, the reaction is stirred for one hour, and the color of the reaction solution is darkened to brown. The reaction solution is poured into a mixture of hydrochloric acid (20 ml)/crashed ice (50 g) with stirring, and the color of the organic phase faded to light yellow to yellow. The organic phase is separated and washed with water (20 ml×3) until aqueous phase is made neutral. After drying over anhydrous $Na_2SO_4$ overnight and filtering out the dessicant, the filter residue is washed with small amount of chloroform, and the filtrate is evaporated to remove the solvent to obtain the product as a light yellow oil. Column chromatography to separate the product (ethyl acetate:petroleum ether=1:400 to about 1:60) as a light yellow oil, which solidified alter standing, with yield of 60%.

3-bromopropionyl-3-benzothiophene (10 mmol), 4-benzylpiperidine (8 mmol), and triethylamine (30 mmol) are dissolved in DMF (50 mL) and operated according to the general synthesis method six to obtain 2.508 of a white solid, with yield of 85.3% (calculated based on 4-benzylpiperidine). MS (m/z): 364.1 $[M+1]^+$.

The product is further reduced with $NaBH_4$ according to the general synthesis method seven, and subjected to silica gel column chromatography separation ($CH_2Cl_2$:MeOH=300:1 to about 100:1). After formation of a hydrochloride, a hydrochloride of V-10 (1.81 g, with yield of 72.1%) is obtained.

Element analysis: $C_{13}H_{28}ClNOS$ (calculated value %: C, 68.72; H, 7.02; N, 3.48; S, 7.98. found value %: C, 68.52; H, 7.00; N, 3.51; S, 8.01).

MS: m/z 366.1 $[M+1]^+$.

Example 8

A hydrochloride of V-11 (Threo-) and of V-12 (Erythro-) 4-(4-fluorobenzyl)-N-[1-methyl-2-hydroxy-2-(5-chloro-6-methoxynaphthalene-2-yl)]ethylpiperidine 2-bromo-1-(5-chloro-6-methoxynaphthalene-2-yl)-acetone (10 mmol 1,4-(4-fluorobenzyl)piperidine (8 mmol), and triethylamine (30 mmol) are dissolved in DMF (50 mL) and operated according to the general synthesis method six to obtain 3.51 g of a white solid, with yield of 92.1%. MS (m/z): 440.0 $[M+1]^+$.

The product is further reduced with $NaBH_4$ according to the general synthesis method seven, and subjected to silica gel column chromatography separation ($CH_2Cl_2$:MeOH=300:1 to about 75:1). After formation of a hydrochloride, a hydrochloride of three-form V-11 (0.68 g, with yield of 19.3%) and a hydrochloride of erythro-form V-12 (1.18 g, with yield of 33.5%) are obtained, respectively.

V-11: MS (m/z): 442.1 $[M+1]^+$. $^1$HNMR ($CDCl_3$): 8.15 (d, J=8.8 Hz, 1H, Ar—H), 7.68 (d, J=11.6 Hz, 1H, Ar—H), 7.52 (dd, J=8.8, 1.6 Hz, 1H, Ar—H), 7.25 (d, 1H, Ar—H), 7.11-22 (m, 4H, Ar—H), 5.13 (br, 1H, disappears upon addition of $D_2O$, >CH—OH), 4.57 (d, J=9.8 Hz, 1H, >CH—OH), 4.03 (s, 3H, —O—$\overline{CH_3}$), 2.86-2.91 (m, 1H, —CH$\overline{CH_3}$), 2.62-2.71 (m, 2H, —N—$\overline{CH_2}$—), 2.51-2.58 (m, $\overline{2H}$, CH—$CH_2$-Ph), 1.72-1.75 (m, $\overline{2H}$, —N—$CH_2$—), 1.54-1.59 (m, 1H, CH—$\overline{CH_2}$-Ph), 1.28-1.45 (m, $\overline{4H}$, —$(CH_2)_2$—CH—), 0.75 (d, J=6.8 Hz, 3H, >CH—$\underline{CH_3}$).

V-12: MS (m/z): 442.1 $[M+1]^+$. $^1$HNMR ($CDCl_3$): 8.15 (d, J=8.8 Hz, 1H, Ar—H), 7.73-7.76 (m, 1H, Ar—H), 7.46 (dd, J=8.8, 1.2 Hz, 1H, Ar—H), 7.26 (d, 1H, Ar—H), 7.12-7.21 (m, 4H, Ar—H), 5.15 (br, 1H, disappears upon addition of $D_2O$, >CH—OH), 4.89 (d, J=4.0 Hz, 1H, >CH—OH), 4.00 (s, 3H, —O—$\overline{CH_3}$), 3.09-3.13 (m, 1H, —CH$\overline{CH_3}$), 2.76-2.82 (m, 2H, —N—$\overline{CH_2}$—), 2.55 (d, J=6.8 Hz, 2H, CH—$CH_2$-Ph), 2.03-2.31 (m, 2H, —N—$CH_2$—), 1.60-2.03 (m, $\overline{2H}$, —$CH_2$—CH—), 1.52-157 (m, 1$\overline{H}$, $\overline{CH}$—$CH_2$-Ph), 1.25-1.35 (m, $\overline{2H}$, —$CH_2$—CH—), 0.83 (d, J=6.8 Hz, 3H, >CH—$\underline{CH_3}$).

Example 9

A hydrochloride of V-13 (Threo-) and of V-14 (Erythro-) 4-benzyl-4-hydroxy-N-[1-methyl-2-hydroxy-2-(5-chloro-6-methoxynaphthalene-2-yl)]ethylpiperidine 2-bromo-1-(5-chloro-6-methoxynaphthalene-2-yl)-acetone (3.28 g, 10 mmol). 4-benzyl-4-hydroxypiperidine (1.5 g, 8 mmol), and triethylamine (3.03 g, 30 mmol) are dissolved in DMF (50 mL) and operated according to the general synthesis method one to obtain 3.05 g of a white solid, with yield of 80.4% (calculated based on 4-benzyl-4-hydroxypiperidine), m.p=228.9-230.4° C. MS (m/z): 438.0 $[M+1]^+$.

The white solid (1.63 g, 3.44 mmol) is dissolved in methanol (30 mL), reduced with $NaBH_4$ according to the general synthesis method seven, and subjected to silica gel column chromatography separation ($CH_2Cl_2$:MeOH=300:1 to about 75:1). After formation of a hydrochloride, a hydrochloride of three-form V-13 (0.62 g, with yield of 37.8%) and a hydrochloride of erythro-form V-14 (0.51 g, with yield of 31.1%) are obtained, respectively.

V-13: m.p=276.6-278.0° C. (decomposition). MS (m/z): 440.3 $[M+1]^+$. $^1$HNMR ($CDCl_3$): 8.20 (d, J=8.8 Hz, 1H, Ar—H), 7.76 (m, 2H, Ar—H), 7.59 (dd, J=1.6, 8.8 Hz, 1H, Ar—H), 7.18-7.36 (m, 6H, Ar—H), 4.41 (d, J=9.6 Hz, 1H, CH—OH), 4.15 (q, 1H, CH$CH_3$), 4.03 (s, 3H, —$OCH_3$), 2.94 (m, 1H, —OH), 2.81 (s, $\overline{2H}$, —$CH_2$-Ph), 2.69-2.73 (m, 2H, —N—$CH_2$—), 2.52-2.57 (m, 2$\overline{H}$, —N—$CH_2$—), 1.51-1.61 (m, 4$\overline{H}$, (—$CH_2$—)$_2$—C—OH), 0.87 (d, J=7.2 Hz, 3H, =CH—$\underline{CH_3}$).

V-14: m.p=271.3-275.0° C. (decomposition). MS (m/z): 440.1 $[M+1]^+$. $^1$HNMR ($CDCl_3$): 11.1 (s, 1H, disappears upon addition of $D_2O$, HCl), 8.15 (d, J=8.8, 1H, Ar—H), 8.12 (s, 1H, Ar—H), 7.81 (d, J=8.8 Hz, 1H, Ar—H), 7.83 (d, J=8.4 Hz, 1H, Ar—H), 7.36 (d, J=8.8 Hz, 1H, Ar—H), 7.21-7.31 (m, 5H, Ar—H), 5.79 (s, 1H, —OH, disappears upon addition of $D_2O$), 4.16 (s, 1H, —OH, disappears upon addition of $D_2O$), 4.02 (s, 3H, —$OCH_3$), 3.77 (d, J=10.4 Hz, 1H, CH—OH), 3.27-3.44 (m, 4H, —N—$(CH_2$—)$_2$), 2.88 (s, 2H, =$\overline{CH_2}$-Ph), 2.35-2.47 (m, 2H, —$CH_2$—C—OH), 1.72-1.77 (m, $\overline{2H}$, —$CH_2$—C—OH), 1.20 (d, J=7.2 Hz, 3H, =CH—$\underline{CH_3}$).

Example 10

A hydrochloride of V-15 (Threo-) and of V-16 (Erythro-) 4-benzyl-4-hydroxy-N-[1-ethyl-2-hydroxy-2-(5-chloro-6-methoxynaphthalene-2-yl)]ethylpiperidine 2-bromo-1-(5-chloro-6-methoxynaphthalene-2-yl)-butanone (10 mm), 4-benzyl-4-hydroxypiperidine (8 mmol), and triethylamine (30 mmol) are dissolved in DMF (50 mL) and operated according to the general synthesis method one to obtain 3.42 g of a white solid, with yield of 87.6% (calculated based on 4-benzyl-4-hydroxypiperidine), m.p=230.1-231.9° C. MS (m/z): 452.1 $[M+1]^+$.

The white solid is dissolved in methanol (30 mL), reduced with $NaBH_4$ according to the general synthesis method seven, and subjected to silica gel column chromatography separation ($CH_2Cl_2$:MeOH=300:1 to about 75:1). After formation of a hydrochloride, a hydrochloride of threo-form V-15 (0.70 g, with yield of 20.4%) and a hydrochloride of erythro-fume V-16 (0.89 g, with yield of 25.9%) are obtained, respectively.

V-15: m.p=278.6-280.7° C. (decomposition). MS (m/z): 454.2 $[M+1]^+$. $^1$HNMR ($CDCl_3$): 8.18 (d, J=8.8 Hz, 1H, Ar—H), 7.78 (m, 2H, Ar—H), 7.58 (dd, J=1.6, 8.8 Hz, 1H, Ar—H), 7.17-7.35 (m, 6H, Ar—H), 4.41 (d, J=9.6 Hz, 1H, CH—OH), 4.15 (t, 1H, CHCH$_2$CH$_3$), 4.03 (s, 3H, —OCH$_3$), 2.94 (m, 1H, —OH), 2.81 (s, 2H, —CH$_2$-Ph), 2.69-2.73 (m, 2H, —N—CH$_2$—), 2.52-2.57 (m, 2H, —N—CH$_2$—) 1.51-1.61 (m, 4H, (—CH$_2$—)$_2$—C—OH), 1.23-1.50 (m, 2H, —CHCH$_2$CH$_3$), 0.75 (d, J=6.8 Hz, 3H, >CHCH$_2$CH$_3$).

V-16: m.p=272.3-278.5° C. (decomposition). MS (m/z): 454.0 $[M+1]^+$. $^1$HNMR ($CDCl_3$): 8.15 (d, J=8.8, 1H, Ar—H), 8.12 (s, 1H, Ar—H), 7.80 (d, J=8.8 Hz, 1H, Ar—H), 7.82 (d, J=8.4 Hz, 1H, Ar—H), 7.39 (d, J=8.8 Hz, 1H, Ar—H), 7.21-7.31 (m, 5H, Ar—H), 4.58 (d, J=4.2 Hz, 1H, CH—OH), 4.18 (t, 1H, CHCH$_2$CH$_3$), 4.02 (s, 3H, —OCH$_3$), 3.27-3.44 (m, 4H, —N—(CH$_2$—)$_2$), 2.88 (s, 2H, —CH$_2$-Ph), 2.35-2.47 (m, 2H, —CH$_2$—C—OH), 1.72-1.77 (m, 2H, —CH$_2$—C—OH), 1.25-1.55 (m, 2H, —CHCH$_2$CH$_3$), 0.83 (d, J=6.8 Hz, 3H, >CH$_2$CH$_3$).

Example 11

A hydrochloride of V-17 (Vireo-) and of V-18 (Erythro-) 4-benzyl-4-hydroxy-N-[1-ethyl-2-hydroxy-2-(benzothiophene-3-yl)]ethylpiperidine 2-bromo-1-(benzothiophene-3-yl)-butanone (10 mmol), 4-benzyl-4-hydroxypiperidine (8 mmol), and triethylamine (30 mmol) are dissolved in DMF (50 mL) and operated according to the general synthesis method one to obtain 2.80 g of a white solid, with yield of 85.6% (calculated based on 4-benzyl-4-hydroxypiperidine). MS (m/z): 394.0 $[M+1]^+$.

The white solid is dissolved in methanol (30 mL), reduced with $NaBH_4$ according to the general synthesis method seven, and subjected to silica gel column chromatography separation ($CH_2Cl_2$:MeOH=300:1 to about 75:1). After formation of a hydrochloride, a hydrochloride of threo-form V-17 (0.63 g, with yield of 22.0%) and a hydrochloride of erythro-form V-18 (0.91 g, with yield of 31.4%) are obtained, respectively.

V-17: MS (m/z): 396.2 $[M+1]^+$. $^1$HNMR ($CDCl_3$): —(dd, 2H, Ar—H), 7.12-7.22 (m, 7H, Ar—H), 6.85 (s, 1H, Ar—H), 1.39 (d, J=9.6 Hz, 1H, CH—OH), 4.17 (t, 1H, CHCH$_2$CH$_3$), 2.81 (s, 2H, —CH$_2$-Ph), 2.69-2.73 (m, 2H, —N—CH$_2$—), 2.52-2.57 (m, 2H, —N—CH$_2$—), 1.51-1.61 (m, 4H, (—CH$_2$—)$_2$—C—OH), 1.25-1.50 (m, 2H, —CHCH$_2$CH$_3$), 0.76 (d, J=6.8 Hz, 3H, >CHCH$_2$CH$_3$).

V-18: MS (m/z): 396.1 $[M+1]^+$. $^1$HNMR ($CDCl_3$): —(dd, 2H, Ar—H), 7.08-7.21 (m, 7H, Ar—H), 6.88 (s, 1H, Ar—H), 4.55 (d, J=4.2 Hz, 1H, CH—OH), 4.16 (t, 1H, CHCH$_2$CH$_3$), 3.27-3.44 (m, 4H, —N—(CH$_2$—)$_2$), 2.88 (s, 2H, —CH CH$_2$H-Ph), 2.35-2.47 (m, 2H, —CH$_2$—C—OH), 1.72-1.77 (m, 2H, —CH$_2$—C—OH), 1.27-1.56 (m, 2H, —CHCH$_2$CH$_3$), 0.85 (d, J=6.8 Hz, 3H, >CHCH$_2$CH$_3$).

Example 12

A hydrochloride of V-19 4-benzyl-4-hydroxy-N-[2-hydroxy-2-(5-chloro-6-methoxynaphthalene-2-yl)] ethylpiperidine 2-bromo-1-(5-chloro-6-methoxynaphthalene-2-yl)-ethanone (10 mmol), 4-benzyl-4-hydroxypiperidine (8 mmol), and triethylamine (30 mmol) are dissolved in DMF (50 mL) and operated according to the general synthesis method one to obtain 3.02 g of a white solid, with yield of 82.1% (calculated based on 4-benzyl-4-hydroxypiperidine), MS (m/z): 424.3 $[M+1]^+$.

The white solid is dissolved in methanol (30 mL), reduced with $NaBH_4$ according to the general synthesis method seven, and subjected to silica gel column chromatography separation ($CH_2Cl_2$:MeOH=300:1 to about 75:1). After formation of a hydrochloride, a hydrochloride of V-19 (1.85 g, with yield of 61.1%) is obtained.

Element analysis: $C_{25}H_{28}ClNO_3 \cdot HCl$ (calculated value %: C, 64.94; H, 6.32; N, 3.03. found value %: C, 65.10; H, 6.33; N, 3.02).

MS: m/z 425.1 $[M+1]^+$.

Example 13

A hydrochloride of V-20 4-benzyl-4-hydroxy-N-[3-hydroxy-3-(5-chloro-6-methoxynaphthalene-2-yl)] propylpiperidine 3-chloro-1-(5-chloro-6-methoxynaphthalene-2-yl)-acetone (10 mmol), 4-benzyl-4-hydroxypiperidine (8 mmol), and triethylamine (30 mmol) are dissolved in DMF (50 mL) and operated according to the general synthesis method one to obtain 3.12 g of a white solid, with yield of 82.3% (calculated based on 4-benzyl-4-hydroxypiperidine), MS (m/z): 438.0 $[M+1]^+$.

The white solid is dissolved in methanol (30 mL), reduced with $NaBH_4$ according to the general synthesis method seven, and subjected to silica gel column chromatography separation ($CH_2Cl_2$:MeOH=300:1 to about 75:1). After formation of a hydrochloride, a hydrochloride of V-20 (2.12 g, with yield of 67.7%) is obtained.

Element analysis: $C_{26}H_{30}ClNO_3 \cdot HCl$ (calculated value %: C, 65.5; H, 6.56; N, 2.94. found value %: C, 65.51; H, 6.55; N, 2.95).

MS: m/z 440.1 $[M+1]^+$.

Example 14

A hydrochloride of V-21 (Threo-) and of V-22 (Erythro-) 4-(4-chlorobenzyl)-4-hydroxy-N-[1-methyl-2-hydroxy-2-(5-chloro-6-methoxynaphthalene-2-yl)]ethylpiperidine 2-bromo-1-(5-chloro-6-methoxynaphthalene-2-yl)-acetone (10 mmol), 4-(4-chlorobenzyl)-4-hydroxypiperidine (8 mmol), and triethylamine (30 mmol) are dissolved in DMF (50 mL) and operated according to the general synthesis method one to obtain 3.20 g of a white solid, with yield of 78.8% [according to 4-(4-chlorobenzyl)-4-hydroxypiperidine], MS (m/z): 472.1 [M+1]$^+$.

The white solid is dissolved in methanol (30 mL), reduced with NaBH$_4$ according to the general synthesis method seven, and subjected to silica gel column chromatography separation (CH$_2$Cl$_2$:MeOH=300:1 to about 75:1). After formation of a hydro chloride, a hydrochloride of threo-form V-21 (0.82 g, with yield of 25.5%) and a hydrochloride of erythro-limn V-22 (1.03 g, with yield of 32.1%) are obtained, respectively.

V-21: MS (m/z): 474.1 [M+1]$^+$. $^1$HNMR (CDCl$_3$): 8.21 (d, J=8.8 Hz, 1H, Ar—H), 8.13 (s, 1H, Ar—H), 7.75 (m, 1H, Ar—H), 7.18-7.36 (m, 3H, Ar—H), 7.02-7.15 (m, 3H, Ar—H), 4.38 (d, J=9.7 Hz, 1H, CH—OH), 4.15 (q, 1H, CHCH$_3$), 4.03 (s, 3H, —OCH$_3$), 2.94 (m, 1H, —OH), 2.81 (s, 2H, —CH$_2$-Ph), 2.69-2.73 (m, —N—CH$_2$—), 2.50-2.57 (m, 2H, —N—CH$_2$—), 1.51-1.61 (m, 4H, (—CH$_2$—)$_2$—C—OH), 0.85 (d, J=7.2 Hz, 3H, =CH—CH$_3$).

V-22: MS (m/z): 474.2 [M+1]$^+$. $^1$HNMR (CDCl$_3$): 8.15 (d, J=8.8, 1H, Ar—H), 8.12 (s, 1H, Ar—H), 7.81 (d, J=8.8 Hz, 1H, Ar—H), 7.21-7.31 (m, 3H, Ar—H), 7.01-7.17 (m, 3H, Ar—H), 4.58 (d, J=4.4 Hz, 1H, CH—OH), 4.17 (q, 1H, CHCH$_3$), 4.02 (s, 3H, —OCH$_3$), 3.76 (d, J=10.4 Hz, 1H, CH—OH), 3.27-3.44 (m, 4H, —N—(CH$_2$—)$_2$), 2.88 (s, 2H, —CH$_2$-Ph), 2.34-2.47 (m, 2H, —CH$_2$—C—OH), 1.70-1.77 (m, 2H, —CH$_2$—C—OH), 1.18 (d, J=7.2 Hz, 3H, =CH—CH$_3$).

Example 15

A hydrochloride of V-23 (Threo-) and V-24 (Erythro-) 4-(4-fluorobenzyl)-4-hydroxy-N-[1-methyl-2-hydroxy-2-(5-chloro-6-methoxynaphthalene-2-yl)]ethylpiperidine 2-bromo-1-(5-chloro-6-methoxynaphthalene-2-yl)-acetone (10 mmol), 4-(4-fluorobenzyl)-4-hydroxypiperidine (8 mmol), and triethylamine (30 mmol) are dissolved in DMF (50 mL), and operated according to the general synthesis method one to obtain 3.51 g of a white solid, with yield of 88.8% [calculated based on 4-(4-fluorobenzyl)-4-hydroxypiperidine], MS (m/z): 456.0 [M+1]$^+$.

The white solid is dissolved in methanol (30 mL), reduced with NaBH$_4$ according to the general synthesis method seven, and subjected to silica gel column chromatography separation (CH$_2$Cl$_2$:MeOH=300:1 to about 75:1). After formation of a hydrochloride, a hydrochloride of threo-form V-23 (1.05 g, with yield of 29.8%) and a hydrochloride of erythro-form V-24 (1.203 g, with yield of 34.91%) are obtained, respectively.

V-23: MS (m/z): 458.1 [M+1]$^+$. $^1$HNMR (CDCl$_3$): 8.21 (d, J=8.8 Hz, 1H, Ar—H), 8.14 (s, 1H, Ar—H), 7.75 (m, 1H, Ar—H), 7.18-7.37 (m, 3H, Ar—H), 7.03-7.16 (m, 3H, Ar—H), 4.37 (d, J=9.7 Hz, 1H, CH—OH), 4.15 (q, 1H, CHCH$_3$), 4.03 (s, 3H, —OCH$_3$), 2.94 (m, 1H, —OH), 2.81 (s, 2H, —CH$_2$-Ph), 2.69-2.73 (m, 2H, —N—CH$_2$—), 2.50-2.57 (m, 2H, —N—CH$_2$—), 1.50-1.61 (m, 4H, (—CH$_2$—)$_2$—C—OH), 0.84 (d, J=7.2 Hz, 3H, =CH—CH$_3$).

V-24: MS (m/z): 4584.2 [M+1]$^+$. $^1$HNMR (CDCl$_3$): 8.17 (d, J=8.8, 1H, Ar—H), 8.12 (s, 1H, Ar—H), 7.80 (d, J=8.8 Hz, 1H, Ar—H), 7.21-7.31 (m, 3H, Ar—H), 7.01-7.16 (m, 3H, Ar—H), 4.58 (d, J=4.4 Hz, 1H, CH—OH), 4.17 (q, 1H, CHCH$_3$), 4.02 (s, 3H, —OCH$_3$), 3.76 (d, J=10.4 Hz, 1H, CH—OH), 3.27-3.44 (m, 4H, —N—(CH$_2$—)$_2$), 2.88 (s, 2H, —CH$_2$-Ph), 2.34-2.47 (m, 2H, —CH$_2$—C—OH), 1.70-1.77 (m, 2H, —CH$_2$—C—OH), 1.15 (d, J=7.2 Hz, 3H, =CH—CH$_3$).

Example 16

A hydrochloride of V-25 (Threo-) and of V-26 (erythro-form) 4-(3,4-dichlorobenzyl)-methylene-N-[1-methyl-2-hydroxy-2-(5-chloro-6-methoxynaphthalene-2-yl)]ethylpiperidine 2-bromo-1-(5-chloro-6-methoxynaphthalene-2-yl)-acetone (1.31 g, 4 mmol), 4-(3,4-dichlorobenzyl)methylenepiperidine hydrochloride (1.05 g, 3.77 mmol), and triethylamine (1.01 g, 10 mmol) are dissolved in DMF (50 mL), and operated according to the general synthesis method one to obtain 1.58 g of a white solid, with yield of 79% [calculated based on 4-(3,4-dichlorine) benzylmethylenepiperidine hydrochloride], m.p=199.2-201.4° C. MS (m/z): 490.1 [M+1]$^+$.

The white solid (1.0 g, 1.9 mmol) is dissolved in methanol (30 mL), reduced with NaBH$_4$ according to the general synthesis method seven, and subjected to silica gel column chromatography separation (CH$_2$Cl$_2$:MeOH=300:1 to about 75:1). After formation of a hydrochloride, a hydrochloride of threo-form V-25 (0.37 g, with yield of 36.9%) and a hydrochloride of erythro-form V-26 (0.21 g, with yield of 21%) are obtained, respectively.

V-25: m.p=240.5-242.5° C. MS (m/z): 490.1 [M+1]$^+$. $^1$HNMR (CDCl$_3$): 12.2 (s, 1H, 1H, HCl, disappears upon addition of D$_2$O), 8.15 (d, J=8.8 Hz, 1H, Ar—H), 7.96 (s, 1H, Ar—H), 7.78 (d, J=9.2 Hz, 1H, Ar—H) 7.68 (d, J=8.8 Hz, 1H, Ar—H), 7.41 (d, J=8.0 Hz, 1H, Ar—H), 7.33 (d, J=9.2 Hz, 1H, Ar—H), 7.28 (d, J=1.0 Hz, 1H, Ar—H), 7.03 (dd, J=8.0, 1.0 Hz, 1H, Ar—H), 6.37 (s, 1H, double bond), 6.02 (s, 1H, CH$_2$CHOH), 5.69 (m, 1H, OH, disappears upon addition of D$_2$O), 4.02 (s, 3H, —OCH$_3$), 3.50-3.51 (m, 1H, CHCH$_3$) 1.17 (s, 3H, —CH$_3$), 2.95-3.46 (m, 8H, CH$_2$).

V-26: m.p=239.5-241.0° C. MS (m/z): 490.0 [M+1]$^+$. $^1$HNMR (CDCl$_3$): 11.0 (s, 1H, HCl, disappears upon addition of D$_2$O), 8.23 (d, J=8.8 Hz, 1H, Ar—H), 7.88 (s, 1H, Ar—H), 7.79 (d, J=9.2 Hz, 1H, Ar—H) 7.73 (d, J=8.8 Hz, 1H, Ar—H), 7.42 (d, J=8.0 Hz, 1H, Ar—H), 7.32 (d, J=8.8 Hz, 1H, Ar—H), 7.28 (d, J=1.0 Hz, 1H, Ar—H), 6.98 (dd, J=8.0, 1.0 Hz, 1H, Ar—H), 6.39 (s, 1H, double bond), 6.02 (d, 1H, OH, disappears upon addition of D$_2$O), 4.73 (d, J=7.6 Hz, 1H, CH$_2$CHOH), 4.09 (q, J=3.2 Hz, 1H, CH$_3$CH), 4.03 (s, 3H, —OCH$_3$), 1.17 (s, 3H, —CH$_3$), 2.97 (m, 8H, CH$_2$).

Example 17

A hydrochloride of V-27 (Threo-) and of V-28 (Erythro-) 4-benzyl-methylene-N-[1-methyl-2-hydroxy-2-(benzothiophene-3-yl)]ethylpiperidine 2-bromo-1-(benzothiophene-3-yl)acetone (4 mmol), 4-benzylmethylenepiperidine hydrochloride (3.77 mmol), and triethylamine (10 mmol) are dissolved in DMF (50 mL), and operated according to the general synthesis method one to obtain 1.02 g of a white solid, with yield of 65.8% (calculated based on 4-benzylmethylenepiperidine hydrochloride). MS (m/z): 362.0 [M+1]$^+$.

The white solid is dissolved in methanol (30 mL), reduced with NaBH$_4$ according to the general synthesis method seven, and subjected to silica gel column chromatography separation (CH$_2$Cl$_2$:MeOH=300:1 to about 75:1). After formation of a hydrochloride, a hydrochloride of threo-form V-27 (0.35 g, with yield of 34.3%) and a hydrochloride of erythro-form V-28 (0.42 g, with yield of 41.2%) are obtained, respectively.

V-27: MS (m/z): 364.1 [M+1]$^+$. $^1$HNMR (CDCl$_3$): —(dd, 2H, Ar—H), 7.12-7.22 (m, 7H, Ar—H), 6.85 (s, 1H, Ar—H), 6.35 (s, 1H, double bond), 4.58 (d, J=9.6 Hz, 1H, CH$_2$CHOH), 4.08 (q, J=3.2 Hz, 1H, CH$_3$CH), 4.02 (s, 3H, —OCH$_3$), 1.17 (s, 3H, —CH$_3$), 2.95-3.46 (m, 8H, CH$_2$).

V-28: MS (m/z): 364.1 [M+1]$^+$. $^1$HNMR (CDCl$_3$): —(dd, 2H, Ar—H), 7.14-7.32 (m, 7H, Ar—H), 6.85 (s, 1H, Ar—H), 6.37 (s, 1H, double bond), 4.73 (d, J=4.2 Hz, 1H, CH$_2$CHOH), 4.09 (q, J=3.2 Hz, 1H, CH$_3$CH), 4.03 (s, 3H, —OCH$_3$), 1.17 (s, 3H, —CH$_3$), 2.97 (m, 8H, CH$_2$).

Example 18

A hydrochloride of V-29 (Threo-) and of V-30 (Erythro-) 4-(3,4-chlorobenzyl)-methylene-N-[1-ethyl-2-hydroxy-2-(5-chloro-6-methoxynaphthalene-2-yl)]ethyl-piperidine 2-bromo-1-(5-chloro-6-methoxynaphthalene-2-yl)-butanone (4 mmol), 4-(3,4-dichlorobenzyl)methylenepiperidine hydrochloride (3.77 mmol), and triethylamine (10 mmol) are dissolved in DMF (50 mL), and operated according to the general synthesis method one to obtain 1.54 g of a white solid, with yield of 75.9% [calculated based on 4-(3,4-dichlorobenzyl)methylenepiperidine hydrochloride], m.p=201.3-204.4° C. MS (m/z): 502.1 [M+1]$^+$.

The white solid is dissolved in methanol (30 mL), reduced with NaBH$_4$ according to the general synthesis method seven, and subjected to silica gel column chromatography separation (CH$_2$Cl$_2$:MeOH=300:1 to about 75:1). After formation of a hydrochloride, a hydrochloride of threo-form V-29 (0.35 g, with yield of 22.7%) and a hydrochloride of erythro-form V-30 (0.44 g, with yield of 28.6%) are obtained, respectively.

V-29: m.p=245.5-248.5° C. MS (m/z): 504.3 [M+1]$^+$. $^1$HNMR (CDCl$_3$): 8.16 (d, J=8.8 Hz, Ar—H), 7.96 (s, 1H, Ar—H), 7.80 (d, J=9.2 Hz, 1H, Ar—H), 7.69 (d, J=8.8 Hz, 1H, Ar—H), 7.41 (d, J=8.0 Hz, 1H, Ar—H), 7.33 (d, J=9.2 Hz, 1H, Ar—H), 7.28 (d, J=1.0 Hz, 1H, Ar—H), 7.03 (dd, J=8.0, 1.0 Hz, 1H, Ar—H), 6.37 (s, 1H, double bond), 4.68 (d, J=9.6 Hz, 1H, CH$_2$CHOH), 4.17 (t, 1H, CH$_3$CH$_2$CH), 4.02 (s, 3H, —OCH$_3$), 2.31-2.39 (m, 2H, CH$_3$CH$_2$), 1.17 (t, 3H, —CH$_3$), 2.95-3.46 (m, 8H, CH$_2$).

V-30: m.p=244.6-247.0° C. MS (m/z): 504.3 [M+1]$^+$. $^1$HNMR (CDCl$_3$): 8.21 (d, J=8.8 Hz, 1H, Ar—H), 7.88 (s, 1H, Ar—H), 7.79 (d, J=9.2 Hz, 1H, Ar—H) 7.73 (d, J=8.8 Hz, 1H, Ar—H), 7.42 (d, J=8.0 Hz, 1H, Ar—H), 7.34 (d, J=8.8 Hz, 1H, Ar—H), 7.28 (d, J=1.0 Hz, 1H, Ar—H), 6.98 (dd, J=8.0, 1.0 Hz, 1H, Ar—H), 6.39 (s, 1H, double bond), 4.73 (d, J=4.2 Hz, 1H, CH$_2$CHOH), 4.19 (t, 1H, Cl$_3$CH$_2$CH), 4.03 (s, 3H, —OCH$_3$), 2.30-2.39 (m, 2H, CH$_3$CH$_2$), 1.17 (t, 3H, —CH$_3$), 2.97 (m, 8H, CH$_2$).

Example 19

A hydrochloride of V-31 4-benzyl-methylene-N-[2-hydroxy-2-(5-chloro-6-methoxynaphthalene-2-yl)]ethylpiperidine 2-bromoacetyl-5-chloro-6-methoxynaphthalene (5 mmol), 4-benzylmethylenepiperidine hydrochloride (4.8 mmol), and triethylamine (10 mmol) am dissolved in DMF (15 mL), and operated according to the general synthesis method one to obtain 2.00 g of a white solid, with yield of 94.5% (calculated based on 4-benzylmethylenepiperidine hydrochloride), MS (m/z): 406.1 [M+1]$^+$.

The obtained white solid is dissolved in methanol (20 mL) and reduced with NaBH$_4$ according to the general synthesis method seven. The reduced product is formed to a salt after formation of a hydrochloride, then 1.38 g of a hydrochloride of V-31 is obtained, with yield of 70.1%. MS (m/z): 408.0 [M+1]$^+$.

$^1$HNMR (CDCl$_3$) δ: 8.15 (d, J=8.8 Hz, 1H, Ar—H), 7.81 (s, 1H, Ar—H), 7.68 (d, J=8.8 Hz, 1H, Ar—H), 7.54 (dd, J=8.8, 1.6 Hz, 1H, Ar—H), 7.30 (m, 4H, Ar—H), 7.14 (m, 2H, Ar—H), 6.47 (s, 1H, double bond) 5.38 (m, 1H, CH$_2$CHOH), 4.02 (s, 3H, —OCH$_3$), 3.42-3.58 (m, 2H, —CHOH—CH$_2$—), 3.20-3.26 (m, 4H, —N—(CH$_2$—)$_2$—), 2.50-2.80 (m, 4H, —(CH$_2$)$_2$—C=).

Example 20

A hydrochloride of V-32

4-benzyl-methylene-N-[3-hydroxy-3-(5-chloro-6-methoxynaphthalene-2-yl)]propylpiperidine 3-chloropropionyl-5-chloro-6-methoxynaphthalene (1.42 g, 5 mmol), 4-benzylmethylenepiperidine hydrochloride (1.01 g, 4.8 mmol), and triethylamine (1.01 g, 10 mmol) are dissolved in DMF (15 mL), and operated according to the general synthesis method one to obtain 2.11 g of a white solid, with yield of 96% (calculated based on 4-benzylmethylenepiperidine hydrochloride), m.p=165.6-166.7° C. MS (m/z): 420.1 [M+1]$^+$.

The obtained white solid (1.5 g, 3.3 mmol) is dissolved in methanol (20 mL) and reduced with NaBH$_4$ according to the general synthesis method seven. The reduced product is funned to a salt after formation of a hydrochloride, and 1.41 g of a hydrochloride of V-32 is obtained, with yield of 94%. m.p=203.3-206.0° C. MS (m/z): 422 [M+1]$^+$.

$^1$HNMR (CDCl$_3$) δ: 12.0 (s, 1H, HCl, disappears upon addition of D$_2$O), 8.17 (d, J=8.8 Hz, 1H, Ar—H), 7.83 (s, 1H, Ar—H), 7.74 (d, J=8.8 Hz, 1H, Ar—H), 7.54 (dd, J=8.8, 1.6 Hz, 1H, Ar—H), 7.30 (m, 4H, Ar—H), 7.14 (m, 2H, Ar—H), 6.47 (s, 1H, double bond) 5.21 (m, 1H, CH$_2$CHOH), 4.02 (s, 3H, —OCH$_3$), 3.20-3.26 (m, 4H, —N—(CH$_2$)$_2$—), 2.97-2.99 (m, 2H, —CH$_2$—CH$_2$—N=), 2.50-2.80 (m, 4H, —(CH$_2$)$_2$—C=), 2.31-2.35 (m, 2H, —CHOH—CH$_2$—).

Example 21

A hydrochloride of V-33 (Threo-) and of V-34 (Erythro-) 4-(4-fluorobenzyl)-methylene-N-[1-methyl-2-hydroxy-2-(5-chloro-6-methoxynaphthalene-2-yl)]ethyl-piperidine 2-bromo-1-(5-chloro-6-methoxynaphthalene-2-yl)-acetone (0.878 g, 2.68 mmol), 4-(4-fluorobenzyl)methylenepiperidine (0.48 g, 2.51 mmol), and triethylamine (0.5 g, 5 mmol) are dissolved in DMF (20 ml), and operated according to the general synthesis method one to obtain 1.06 g of a white solid, with yield of 89% [calculated based on 4-(4-fluorobenzyl)methylenepiperidine], m.p=168.4-170.9° C. MS (m/z): 438.1 [M+1]$^+$.

The obtained white solid (b 1.0 g, 2.1 mmol) is dissolved in methanol (30 ml), reduced with NaBH$_4$ according to the general synthesis method seven, and subjected to silica gel column chromatography separation (CH$_2$Cl$_2$:MeOH=300:1 to about 75:1). After formation of a hydrochloride, a hydrochloride of threo-form V-33 (0.16 g, with yield of 16%) and a hydrochloride of erythro-form V-34 (0.30 g, with yield of 30%) are obtained, respectively.

V-33: m.p=217.6-219.0° C. MS (m/z): 440.2 [M+1]$^+$.
$^1$HNMR (CDCl$_3$) δ: 10.9 (s, 1H, disappears upon addition of D$_2$O, HCl), 8.25 (d, J=8.8 Hz, 1H, Ar—H), 7.89 (s, 1H, Ar—H), 7.80 (d, J=8.8 Hz, 1H, Ar—H), 7.70 (d, J=8.8 Hz, 1H, Ar—H), 7.34 (d, J=5.6 Hz, 1H, Ar—H), 7.03-7.16 (m, 4H, Ar—H), 6.45 (s, 1H, =CH-Ph), 4.73 (s, 1H, >CH—CH, disappears upon addition of D$_2$O), 4.12 (d, J=9.2 Hz, >CH—OH), 4.03 (s, 3H, —O—CH$_3$), 3.55-4.03 (m, 4H, =N—(CH$_2$—)$_2$—), 2.80-3.00 (m, 4H, —(CH$_2$—)$_2$=CH—), 1.00 (d, J=6.8 Hz, 3H, >CH—CH$_3$).

V-34: m.p=223.5-225.4° C. MS (m/z): 440.1 [M+1]$^+$.
$^1$HNMR (CDCl$_3$): 11.60 (s, 1H, disappears upon addition of D$_2$O, HCl), 8.14 (d, J=8.8 Hz, 1H, Ar—H), 7.96 (s, 1H, Ar—H), 7.83 (d, J=8.8 Hz, 1H, Ar—H), 7.73 (d, J=8.8 Hz, 1H, Ar—H), 7.40 (d, J=8.8 Hz, 1H, Ar—H), 7.18-7.21 (m, 2H, Ar—H), 7.03-7.0 (m, 2H, Ar—H), 6.44 (s, 1H, =CH-Ph), 4.04 (m, 1H, >CH—OH), 4.03 (s, 3H, —O—CH$_3$), 3.55-3.56 (m, 4H, —N—(CH$_2$—)$_2$—), 2.97-3.12 (m, 2H, —(CH$_2$—)$_2$=CH—), 0.99 (d, J=6.8 Hz, 3M, >CH—CH$_3$).

Example 22

A hydrochloride of V-35 (Threo-) and of V-36 (Erythro-) 4-(4-chlorobenzyl)-methylene-N-[1-methyl-2-hydroxy-2-(5-chloro-6-methoxynaphthalene-2-yl)]ethyl-piperidine 2-bromo-1-(5-chloro-6-methoxynaphthalene-2-yl)-acetone (2.68 mmol), 4-(4-chlorobenzyl)methylenepiperidine (2.51 mmol), and triethylamine (5 mmol) are dissolved in DMF (20 ml), and operated according to the general synthesis method one to obtain 1.16 g of a white solid, with yield of 88.2% [calculated based on 4-(4-chlorobenzyl)methylenepiperidine], m.p=167.5-170.8° C. MS (m/z): 454.1 [M+1]$^+$.

The obtained white solid is dissolved in methanol (30 ml), reduced with NaBH$_4$ according to the general synthesis method seven, and subjected to silica gel column chromatography separation (CH$_2$Cl$_2$:MeOH=300:1 to about 75:1). After formation of a hydrochloride, a hydrochloride of threo-form V-35 (0.25 g, with yield of 21.5%) and a hydrochloride of erythro-form V-36 (0.30 g, with yield of 25.9%) are obtained, respectively.

V-35: m.p=217.8-219.5° C. MS (m/z): 456.2 [M+1]$^+$.
$^1$HNMR (CDCl$_3$) δ: 8.21 (d, J=8.8 Hz, 1H, Ar—H), 7.88 (s, 1H, Ar—H), 7.80 (d, J=8.8 Hz, 1H, Ar—H), 7.70 (d, J=8.8 Hz, 1H, Ar—H), 7.34 (d, J=5.6 Hz, 1H, Ar—H), 7.03-7.16 (m, 4H, Ar—H), 6.45 (s, 1H, =CH-Ph), 4.73 (s, 1H, >CH—OH, disappears upon addition of D$_2$O), 4.12 (d, J=9.2 Hz, >CH—OH), 4.03 (s, 3H, —O—CH$_3$), 3.55-4.03 (m, 4H, =N—(CH$_2$—)$_2$—), 2.80-3.00 (m, 4H, —(CH$_2$—)$_2$=CH—), 1.00 (d, J=6.8 Hz, 3H, >CH—CH$_3$).

V-36: m.p=222.5-225.9° C. MS (m/z): 456.1 [M+1]$^+$.
$^1$HNMR (CDCl$_3$): 8.14 (d, J=8.8 Hz, 1H, Ar—H), 7.96 (s, 1H, Ar—H), 7.83 (d, J=8.8 Hz, 1H, Ar—H), 7.72 (d, J=8.8 Hz, 1H, Ar—H), 7.40 (d, J=8.8 Hz, 1H, Ar—H), 7.18-7.21 (m, 2H, Ar—H), 7.03-7.07 (m, 2H, Ar—H), 6.44 (s, 1H, =CH-Ph), 4.04 (m, 1H, >CH—OH), 4.03 (s, 3H, —O—CH$_3$), 3.55-3.56 (m, 4H, —N—(CH$_2$—)$_2$—), 2.97-3.12 (m, 4H, —(CH$_2$—)$_2$=CH—), 0.99 (d, J=6.8 Hz, 3H, >CH—CH$_3$).

Example 23

A hydrochloride of V-37 (Threo-) and of V-38 (Erythro-) 4-benzyl-methylene-N-[1-methyl-2-hydroxy-2-(5-chloro-6-methoxynaphthalene-2-yl)]ethyl-piperidine 2-bromo-1-(5-chloro-6-methoxynaphthalen-2-yl)-acetone (2.44 g, 7.45 mmol), 4-benzylmethylenepiperidine hydrochloride (1.25 g, 5.96 mmol), and triethylamine (2.02 g, 20 mmol) are dissolved in DMF (50 ml) and operated according to the general synthesis method one to obtain 2.18 g of a white solid, with yield of 80% (calculated based on 4-benzyl-methylenepiperidine hydrochloride), m.p=177.3-180.0° C. MS (m/z): 420.2 [M+1]$^+$.

The white solid (2.0 g, 4.38 mmol) is dissolved in methanol (50 ml), reduced with NaBH$_4$ according to the general synthesis method seven, and subjected to silica gel column chromatography separation CH$_2$Cl$_2$:MeOH=300:1 to about 75:1). After formation of a hydrochloride, a hydrochloride of threo-form V-37 (0.53 g, with yield of 26.4%) and a hydrochloride of erythro-form V-38 (0.85 g, with yield of 42.3%) are obtained, respectively.

V-37: m.p=211.0-213.0° C. MS (m/z): 422.1 [M+1]$^+$.
$^1$HNMR (CDCl$_3$): 8.15 (d, 10.8 (s, 1H, disappears upon addition of D$_2$O, HCl), 8.24 (d, J=8.8 Hz, 1H, Ar—H), 7.89 (s, 1H, Ar—H), 7.79 (d, J=8.8 Hz, 1H, Ar—H), 7.70 (d, J=8.8 Hz, 1H, Ar—H), 7.27-7.34 (m, 3H, Ar—H), 7.22-7.27 (m, 1H, Ar—H), 7.15-7.17 (m, 2H, Ar—H), 6.10 (s, 1H, =CH-Ph), 4.72 (s, 1H, >CH—OH), 4.02 (s, 3H, —O—CH$_3$), 2.80-3.20 (m, 4H, —N—(CH$_2$)$_2$—), 2.40-2.70 (m, 4H, —(CH$_2$—)$_2$=CH—), 1.09 (d, J=6.4 Hz, 3H, >CH—CH$_3$).

V-38: m.p=211.0-213.0° C. MS (m/z): 422.1 [M+1]$^+$.
$^1$HNMR (CDCl$_3$): 12.05 (s, 1H, disappears upon addition of D$_2$O, HCl), 8.17 (d, J=8.8 Hz, 1H, Ar—H), 7.97 (s, 1H, Ar—H), 7.81 (d, J=9.2 Hz, 1H, Ar—H), 7.75 (d, J=8.4 Hz, 1H, Ar—H), 7.32-736 (m, 3H, Ar—H), 7.24-7.26 (m, 1H, Ar—H), 7.17-7.19 (m, 2H, Ar—H), 6.47 (s, 1H, =CH-Ph), 6.03 (m, 1H, >CH—OH), 6.65 (s, 1H, >CH—OH), 4.03 (s, 3H, —O—CH$_3$), 3.49-3.51 (m, 1H, >CH—CH$_3$), 3.01-3.20 (m, 4H, —N—(CH$_2$)$_2$—), 2.50-3.00 (m, 4H, —(CH$_2$—)$_2$=CH—), 1.22 (d, J=7.2 Hz, 3H, >CH—CH$_3$).

Example 24

A hydrochloride of V-39 (Threo-) and of V-40 (Erythro-) 4-benzyl-N-[1-methyl-2-hydroxy-2-(5-chloro-6-methoxynaphthalene-2-yl)]ethyl-1,2,3,6-tetrahydropyridine 2-bromo-1-(5-chloro-6-methoxynaphthalene-2-yl)-acetone (3.28 g, 10 mmol).

4-benzyl-1,2,3,6-tetrahydropyridine hydrochloride (1.89 g, 9 mmol), and triethylamine (3.03 g, 30 mmol) are dissolved in DMF (50 ml), and operated according to the general synthesis method one to obtain 3.88 g a white solid, with yield of 94% (calculated based on 4-benzyl-1,2,3,6-tetrahydropyridine hydrochloride), m.p=226.4-228.0° C. MS (m/z): 420.1 [M+1]$^+$.

The white solid (2.0 g, 4.38 mmol) is dissolved in methanol (50 ml), reduced with NaBH$_1$ according to the general synthesis method seven method B, and subjected to silica gel chromatography separation (CH$_2$Cl$_2$:MeOH=300:1 to about 75:1). After formation of a hydrochloride, a hydrochloride of threo-form V-39 (0.81 g, with yield of 40.3%) and a hydrochloride of erythro-form V-40 (0.75 g, with yield of 37.4%) are obtained, respectively.

V-39: m.p=250.6-252.4° C. MS (m/z): 422.2 [M+1]$^+$.
$^1$HNMR (CDCl$_3$): 10.51 (s, 1H, disappears upon addition of D$_2$O, HCl), 8.24 (d, J=8.8 Hz, 1H, Ar—H), 7.90 (s, 1H, Ar—H), 7.80 (d, J=8.8 Hz, 1H, Ar—H), 7.71 (dd, J=1.6, 8.8 Hz, 1H, Ar—H), 7.30-7.34 (m, 3H, Ar—H), 7.22-7.24 (m, 1H, Ar—H), 7.16 (m, 2H, Ar—H), 6.01 (s, 1H, >CH—OH, disappears upon addition of D$_2$O), 5.45 (s, 1H, —CH=), 4.64 (m, 1H, >CH—OH), 4.21 (m, 1H, CHCH$_3$), 4.03 (s, 3H, —O—CH$_3$), 3.40 (s, 1H, —CH$_2$-Ph), 2.08-3.90 (m, 6H, piperidine), 1.10 (d, J=6.8 Hz, =CH—CH$_3$).

V-40: m.p=253.7-255.8° C. MS (m/z): 422.1 [M+1]$^+$. $^1$HNMR (CDCl$_3$): 8.15 (d, J=9.2 Hz, 1H, Ar—H), 7.94 (s, 1H, Ar—H), 7.80 (d, J=8.8 Hz, 1H, Ar—H), 7.70 (d, J=8.8 Hz, 1H, Ar—H), 7.28-7.33 (m, 3H, Ar—H), 7.19-7.24 (m, 3H, Ar—H), 5.85 (s, 1H, >CH—OH), 5.46 (s, 1H, —CH=), 4.03 (s, 3H, —O—CH$_3$), 3.78-3.81 (m, 1H, >CH—OH), 3.48-3.51 (m, 1H, CHCH$_3$), 3.40 (s, 1H, —CH$_2$-Ph), 2.79-2.82 (m, 6H, piperidine), 1.19 (d, J=7.2 Hz, =CH—CH$_3$).

Example 25

A hydrochloride of V-41 (Threo-) and of V-42 (Erythro-) 4-benzyl-N-[1-methyl-2-hydroxy-2-(benzothiophene-3-yl)]ethyl-1,2,3,6-tetrahydropyridine 2-bromo-1-(benzothiophene-3-yl)-acetone (10 mmol), 4-benzyl-1,2,3,6-tetrahydropyridine hydrochloride (9 mmol), and triethylamine (30 mmol) are dissolved in DMF (50 ml), and operated according to the general synthesis method one to obtain 2.95 g of a white solid, with yield of 82.3% (calculated based on 4-benzyl-1,2,3,6-tetrahydropyridine hydrochloride). MS (m/z): 362.0 [M+1]$^+$.

The % white solid is dissolved in methanol (50 ml), reduced with NaBH$_4$ according to the general synthesis method seven method B, and subjected to silica gel column chromatography (CH$_2$Cl$_2$:MeOH=300:1 to about 75:1). After formation of a hydrochloride, a hydrochloride of threo-form V-41 (0.78 g, with yield of 24.5%) and a hydrochloride of erythro-form V-42 (0.82 g, with yield of 25.7%) are obtained, respectively.

V-41: MS (m/z): 364.2 [M+1]$^+$. $^1$HNMR (CDCl$_3$): —(dd, 2H, Ar—H), 7.14-7.25 (m, 7H, Ar—H), 6.88 (s, 1H, Ar—H), 5.45 (s, 1H, —CH=), 4.64 (m, 1H, >CH—OH), 4.21 (m, 1H, CHCH$_3$), 4.03 (s, 3H, —O—CH$_3$), 3.40 (s, 1H, —CH$_2$-Ph), 2.08-3.90 (m, 6H, piperidine), 1.08 (d, J=6.8 Hz, =CH—CH$_3$).

V-42: MS (m/z): 364.1 [M+1]$^+$. $^1$HNMR (CDCl$_3$): —(dd, 2H, Ar—H), 7.12-7.22 (m, 7H, Ar—H), 6.85 (s, 1H, Ar—H), 5.85 (s, 1H, >CH—OH), 5.46 (s, 1H, —CH=), 4.03 (s, 3H, —O—CH$_3$), 3.78-3.81 (m, 1H, >CH—OH), 3.48-3.51 (m, 1H, CHCH$_3$), 3.40 (s, 1H, —CH$_2$-Ph), 2.79-2.82 (m, 6H, piperidine), 1.17 (d, J=7.2 Hz, =CH—CH$_3$).

Example 26

A hydrochloride of V-43 (Threo-) and of V-44 (Erythro-) 4-benzyl-N-[1-ethyl-2-hydroxy-2-(5-chloro-6-methoxynaphthalene-2-yl)]ethyl-1,2,3,6-tetrahydropyridine 2-bromo-1-(5-chloro-6-methoxynaphthalene-2-yl)-Butanone (10 mmol), 4-benzyl-1,2,3,6-tetrahydropyridine hydrochloride (9 mmol), and triethylamine (30 mmol) are dissolved in DMF (50 ml), and operated according to the general synthesis method one to obtain 3.92 g of a white solid, with yield of 93.5% (calculated based on 4-benzyl-1,2,3,6-tetrahydropyridine hydrochloride), m.p=228.2-232.5° C. MS (m/z): 434.1 [M+1]$^+$.

The white solid is dissolved in methanol (50 ml), reduced with NaBH$_4$ according to the general synthesis method seven method B, and subjected to silica gel column chromatography (CH$_2$Cl$_2$:MeOH=300:1 to about 75:1). After formation of a hydrochloride, a hydrochloride of threo-form V-43 (0.90 g, with yield of 22.9%) and a hydrochloride of erythro-form V-44 (1.21 g, with yield of 30.5%) are obtained, respectively.

V-43: m.p=252.3-256.2° C. MS (m/z): 436.0 [M+1]$^+$. $^1$HNMR (CDCl$_3$): 8.25 (d, J=8.8 Hz, 1H, Ar—H), 7.92 (s, 1H, Ar—H), 7.80 (d, J=8.8 Hz, 1H, Ar—H), 7.71 (dd, J=1.6, 8.8 Hz, 1H, Ar—H), 7.30-7.34 (m, 3H, Ar—H), 7.20-7.24 (m, 1H, Ar—H), 7.16 (m, 2H, Ar—H), 5.45 (s, 1H, —CH=), 4.64 (m, 1H, >CH—OH), 4.21 (t, 1H, CH$_2$CH$_2$CH$_3$), 4.03 (s, 3H, —O—CH$_3$), 3.40 (s, 1H, —CH$_2$-Ph), 2.08-3.90 (m, 6H, piperidine), 1.59 (m, 2H, CH$_2$CH$_3$) 1.19 (t, 3H, CH$_2$—CH$_3$).

V-44: m.p=253.7-257.9° C. MS (m/z): 436.0 [M+1]$^+$, $^1$HNMR (CDCl$_3$): 8.15 (d, J=9.2 Hz, 1H, Ar—H), 7.93 (s, 1H, Ar—H), 7.81 (d, J=8.8 Hz, 1H, Ar—H), 7.70 (d, J=8.8 Hz, 1H, Ar—H), 7.28-7.35 (m, 3H, Ar—H), 7.19-7.24 (m, 3H, Ar—H), 5.85 (s, 1H, >CH—OH), 5.46 (s, 1H, —CH=), 4.03 (s, 3H, —O—CH$_3$), 3.78-3.81 (m, 1H, >CH—OH), 3.48-3.51 (t, 1H, CHCH$_2$CH$_3$), 3.40 (s, 1H, —CH$_2$-Ph), 2.79-2.82 (m, 6H, piperidine), 1.59 (m, 2H, CH$_2$CH$_3$) 1.19 (t, 3H, CH$_2$—CH$_3$).

Example 27

A hydrochloride of V-45 4-benzyl-N-[2-hydroxy-2-(5-chloro-6-methoxynaphthalene-2-yl)]ethyl-1,2,3,6-tetrahydropyridine 2-bromo-1-(5-chloro-6-methoxynaphthalene-2-yl)-ethanone (10 mmol), 4-benzyl-1,2,3,6-tetrahydropyridine hydrochloride (9 mmol), and triethylamine (30 mmol) are dissolved in DMF (50 ml), and operated according to the general synthesis method one to obtain 3.50 g of a white solid, with yield of 88.0% (calculated based on 4-benzyl-1,2,3,6-tetrahydropyridine hydrochloride). MS (m/z): 406.1 [M+1]$^+$.

The white solid is dissolved in methanol (50 ml), reduced with NaBH$_4$ according to the general synthesis method seven method B, and subjected to silica gel column chromatography (CH$_2$Cl$_2$:MeOH=300:1 to about 75:1). After formation of a hydrochloride, a hydrochloride of V-45 (2.50 g, with yield of 71.2%) is obtained.

Element analysis: C$_{25}$H$_{26}$ClNO$_2$·HCl (calculated value %: C, 67.57; H, 6.12; N, 3.15. found value %: C, 67.54; H, 6.11; N, 3.15).

MS: m/z 408.1 [M+1]$^+$.

Example 28

A hydrochloride of V-46 4-benzyl-N-[3-hydroxy-3-(5-chloro-6-methoxynaphthalene-2-yl)]propyl-1,2,3,6-tetrahydropyridine 3-chloro-1-(5-chloro-6-methoxynaphthalene-2-yl)-acetone (10 mmol), 4-benzyl-1,2,3,6-tetrahydropyridine hydrochloride (9 mmol), and triethylamine (30 mmol) are dissolved in DMF (50 ml), and operated according to the general synthesis method one to obtain 3.89 g of a white solid, with yield of 94.6% (calculated based on 4-benzyl-1,2,3,6-tetrahydropyridine hydrochloride) MS (m/z): 420.0 [M+1]$^+$.

The white solid is dissolved in methanol (50 ml), reduced with NaBH$_4$ according to the general synthesis method seven method B, and subjected to silica gel column chromatography (CH$_2$Cl$_2$:MeOH=300:1 to about 75:1). After formation of a hydrochloride, a hydrochloride of V-46 (2.62 g, with yield of 67.2%) is obtained.

Element analysis: C$_{26}$H$_{28}$ClNO$_2$·HCl (calculated value %: C, 68.12; H, 6.38; N, 3.06. found value %: C, 68.14; H, 6.39; N, 3.06).

MS m/z 422.1 [M+1]$^+$.

Example 29

A hydrochloride of V-47 (Threo-) and of V-48 (Erythro-)

4-(4-fluorobenzyl)-N-[1-methyl-2-hydroxy-2-(5-chloro-6-methoxynaphthalene-2-yl)]ethyl-1,2,3,6-tetrahydropyridine 2-bromo-1-(5-chloro-6-methoxynaphthalene-2-yl)-acetone (10 mmol), 4-(4-fluorobenzyl)-1,2,3,6-tetrahydropyridine hydrochloride (9 mmol), and triethylamine (30 mmol) are dissolved in DMF (50 ml), and operated according to the general synthesis method one to obtain 3.85 g of a white solid, with yield of 90.2% [calculated based on 4-(4-fluorobenzyl)-1,2,3,6-tetrahydropyridine hydrochloride], m.p=228.4-230.5° C. MS (m/z): 438.1 [M+1]$^+$.

The white solid is dissolved in methanol (50 ml), reduced with NaBH$_4$ according to the general synthesis method seven method B, and subjected to silica gel column chromatography (CH$_2$Cl$_2$:MeOH=300:1 to about 75:1). After formation of a hydrochloride, a hydrochloride of threo-form V-47 (1.12 g, with yield of 29.0%) and a hydrochloride of erythro-form V-48 (1.23 g, with yield of 31.9%) are obtained, respectively.

V-47: m.p=254.3-257.6° C. MS (m/z): 440.0 [M+1]$^+$. $^1$HNMR (CDCl$_3$): 8.25 (d, J=8.8 Hz, 1H, Ar—H), 7.90 (s, 1H, Ar—H), 7.80 (d, J=8.8 Hz, 1H, Ar—H), 7.71 (dd, J=1.6, 8.8 Hz, 1H, Ar—H), 7.30-7.34 (m, 2H, Ar—H), 7.22-7.24 (m, 3H, Ar—H), 5.45 (s, 1H, —CH=), 4.64 (m, 1H, >CH—OH), 4.21 (m, 1H, CHCH$_3$), 4.03 (s, 3H, —O—CH$_3$), 3.40 (s, 1H, —CH$_2$-Ph), 2.08-3.90 (m, 6H, piperidine), 1.10 (d, J=6.8 Hz, =CH—CH$_3$).

V-48: m.p=255.2-258.3° C. MS (m/z): 440.0 [M+1]$^+$. $^1$HNMR (CDCl$_3$): 8.17 (d, J=9.2 Hz, 1H, Ar—H), 7.94 (s, 1H, Ar—H), 7.80 (d, J=8.8 Hz, 1H, Ar—H), 7.70 (d, J=8.8 Hz, 1H, Ar—H), 7.28-7.33 (m, 2H, Ar—H), 7.19-7.24 (m, 3H, Ar—H), 5.85 (s, 1H, >CH—OH), 5.46 (s, 1H, —CH=), 4.03 (s, 3H, —O—CH$_3$), 3.78-3.81 (m, 1H, >CH—OH), 3.48-3.51 (m, 1H, CHCH$_3$), 3.40 (s, 1H, —CH$_2$-Ph), 2.79-2.82 (m, 6H, piperidine), 1.18 (d, J=7.2 Hz, =CH—CH$_3$).

Example 30

A hydrochloride of V-49 (Threo-) and of V-50 (Erythro-) 4-benzyloxy-N-[1-methyl-2-hydroxy-2-(5-chloro-6-methoxynaphthalene-2-yl)]ethyl-piperidine 2-bromo-1-(5-chloro-6-methoxynaphthalene-2-yl)-acetone (1.64 g, 5 mmol), 4-benzyloxypiperidine (0.862 g, 4.51 mmol), and triethylamine (1.01 g, 10 mmol) are dissolved in DMF (20 ml), and operated according to the general synthesis method one to obtain 2.07 g of a white solid, with yield of 96.7% (calculated based on 4-benzyloxypiperidine), m.p=152.2-155.0° C. MS (m/z): 438.2 [M+1]$^+$.

The white solid (1.50 g, 3.16 mmol) is reduced with aluminium isopropoxide according to the general synthesis method seven method A, and subjected to silica gel column chromatography (CH$_2$Cl$_2$:MeOH=300:1 to about 75:1). After formation of a hydrochloride, a hydrochloride of threo-form V-49 (0.58 g, with yield of 39%) and a hydrochloride of erythro-form V-50 (0.32 g, with yield of 21%) are obtained, respectively.

V-49: m.p=197.4-199.7° C. MS (m/z): 440.2 [M+1]$^+$. $^1$HNMR (CDCl$_3$): 10.41 (s, 1H, disappears upon addition of D$_2$O, HCl), 8.24 (d, J=8.8 Hz, 1H, Ar—H), 7.78 (s, 1H, Ar—H), 7.80 (d, J=9.2 Hz, 1H, Ar—H), 7.66-7.73 (m, 2H, Ar—H), 7.51-7.53 (m, 1H, Ar—H), 7.31-7.39 (m, 4H, Ar—H), 6.06 (s, 1H, >CH—OH, disappears upon addition of D$_2$O), 4.72 (s, 2H, —O—CH-Ph), 4.10 (d, J=6.8 Hz, 1H, >CH—OH), 4.03 (s, 3H, —O—CH$_3$), 3.77-3.78 (m, 1H, >CH—CH$_3$), 3.28-3.35 (m, 4H, —N—(CH$_2$)$_2$—), 2.16-2.44 (m, 4H, —(CH$_2$)$_2$—CH—O—), 2.65-2.67 (m, 1H, —(CH$_2$)$_2$—CH—O—), 1.00 (d, J=6.8 Hz, 3H, >CH—CH$_3$)

V-50: m.p=204.5-207.3° C. MS (m/z): 440.3 [M+1]$^+$. $^1$HNMR (CDCl$_3$): 11.5 (s, 1H, disappears upon addition of D$_2$O, HCl), 8.09 (d, J=8.8 Hz, 1H, Ar—H), 7.87 (s, 1H, Ar—H), 7.66-7.73 (m, 2H, Ar—H), 7.56 (d, J=8.8 Hz, 1H, Ar—H), 7.51-7.53 (m, 1H, Ar—H), 7.23-7.37 (m, 4H, Ar—H), 4.50 (s, 2H, —O—CH$_2$-Ph), 4.10 (d, J=2.4 Hz, >CH—OH), 4.01 (s, 3H, —O—CH$_3$), 3.79-3.81 (m, 1H, >CH—CH$_3$), 3.30-3.32 (m, 4H, —N—(CH$_2$)$_2$—), 2.40-2.60 (m, 4H, —(CH$_2$)$_2$—CH—O), 2.02-2.08 (m, 1H, —(CH$_2$)$_2$—CH—O—), 1.19 (d, J=6.4 Hz, 3H, >CH—CH$_3$).

Example 31

A hydrochloride of V-51 (Threo-) and of V-52 (Erythro-) 4-benzyloxy-N-[1-methyl-2-hydroxy-2-(benzothiophene-3-yl)]ethylpiperidine 2-bromo-1-(benzothiophene-3-yl)-acetone (5 mmol), 4-benzyloxy piperidine (4.51 mmol), and triethylamine (10 mmol) are dissolved in DMF (20 ml), and operated according to the general synthesis method one to obtain 1.50 g a white solid, with yield of 86.2% (calculation according to 4-benzyloxypiperidine), MS (m/z): 380.0 [M+1]$^+$.

The white solid (1.50 g, 3.16 mmol) is reduced with aluminium isopropoxide according to the general synthesis method seven method A, and subjected to silica gel column chromatography (CH$_2$Cl$_2$:MeOH=300:1 to about 75:1). After formation of a hydrochloride, a hydrochloride of threo-form V-51 (0.52 g, with yield of 32.4%) and a hydrochloride of erythro-form V-52 (0.53 g, with yield of 33.1%) are obtained, respectively.

V-51: MS (m/z): 382.2 [M+1]$^+$. $^1$HNMR (CDCl$_3$): —(dd, 2H, Ar—H), 7.14-7.25 (m, 7H, Ar—H), 6.88 (s, 1H, Ar—H), 4.72 (s, 2H, —O—CH$_2$-Ph), 4.10 (d, J=6.8 Hz, 1H, >CH—OH), 3.77-3.78 (m, 1H, >CH—CH$_3$), 3.28-3.35 (m, 4H, —N—(CH$_2$)$_2$—), 2.16-2.44 (m, 4H, —(CH$_2$)$_2$—CH—O—), 2.65-2.67 (m, 1H, —(CH$_2$)$_2$—CH—O—), 1.03 (d, J=6.8 Hz, 3H, >CH—CH$_3$).

V-52: MS (m/z): 382.2 [M+1]$^+$. $^1$HNMR (CDCl$_3$): —(dd, 2H, Ar—H), 7.16-7.25 (m, 7H, Ar—H), 6.85 (s, 1H, Ar—H), 4.50 (s, 2H, —O—CH$_2$-Ph), 4.10 (d, J=2.4 Hz, >CH—OH), 3.79-3.81 (m, 1H, >CH—CH$_3$), 3.30-3.32 (m, 4H, —N—(CH$_2$)$_2$—), 2.40-2.60 (m, 4H, —(CH$_2$)$_2$—CH—O), 2.02-2.08 (m, 1H, —(CH$_2$)$_2$—CH—O—), 1.15 (d, J=6.4 Hz, 3H, >CH—CH$_3$).

Example 32

A hydrochloride of V-53 (Threo-) and of V-54 (Erythro-) 4-benzyloxy-N-[1-ethyl-2-hydroxy-2-(5-chloro-6-methoxynaphthalene-2-yl)]ethyl-piperidine 2-bromo-1-(5-chloro-6-methoxynaphthalene-2-yl)-Butanone (5 mmol), 4-benzyloxypiperidine (4.51 mmol), and triethylamine (10 mmol) are dissolved in DMF (20 ml), and operated according to the general synthesis method one to obtain 2.10 g of a white solid, with yield of 96.5% (calculated based on 4-benzyloxypiperidine), m.p=155.2-158.6° C. MS (m/z): 452.0 [M+1]$^+$.

The white solid is reduced with aluminium isopropoxide according to the general synthesis method seven method A, and subjected to silica gel column chromatography (CH$_2$Cl$_2$MeOH=300:1 to about 75:1). After formation of a hydrochloride, a hydrochloride of threo-form V-53 (0.52 g, with yield of 24.6%) and a hydrochloride of erythro-form V-54 (0.48 g, with yield of 22.7%) are obtained, respectively.

V-53: m.p=199.2-203.5° C. MS (m/z): 454.2 [M+1]$^+$. $^1$HNMR (CDCl$_3$): 8.23 (d, J=8.8 Hz, 1H, Ar—H), 7.78 (s, 1H, Ar—H), 7.80 (d, J=9.2 Hz, 1H, Ar—H), 7.66-7.73 (m, 2H, Ar—H), 7.51-7.53 (m, 1H, Ar—H), 7.31-7.39 (m, 4H, Ar—H), 4.72 (s, 2H, —O—CH$_2$-Ph), 4.10 (d, J=6.8 Hz, 1H, >CH—OH), 4.03 (s, 3H, —O—CH$_3$), 3.77-3.78 (t, 1H, >CH—CH$_2$CH$_3$), 3.28-3.35 (m, 4H, —N—(CH$_2$)$_2$—), 2.16-2.44 (m, 4H, —(CH$_2$)$_2$—CH—O—), 2.65-2.67 (m, 1H, —(CH$_2$)$_2$—CH—O—), 1.85-1.92 (m, 2H, >CH—CH$_2$), 1.00 (t, J=6.4 Hz, 3H, >CHCH$_2$—CH$_3$).

V-54: m.p=207.2-209.9° C. MS (m/z): 454.2 [M+1]$^+$. $^1$HNMR (CDCl$_3$): 8.19 (d, J=8.8 Hz, 1H, Ar—H), 7.87 (s, 1H, Ar—H), 7.66-7.73 (m, 2H, Ar—H), 7.56 (d, J=8.8 Hz, 1H, Ar—H), 7.51-7.53 (m, 1H, Ar—H), 7.23-7.37 (m, 4H, Ar—H), 4.50 (s, 2H, —O—CH$_2$-Ph), 4.10 (d, J=2.4 Hz, >CH—OH), 4.01 (s, 3H, —O—CH$_3$), 3.79-3.81 (t, 1H, >CH—CH$_2$CH$_3$), 3.30-3.32 (m, 4H, —N—(CH$_2$)$_2$—), 2.40-2.60 (m, 4H, —(CH$_2$)$_2$—CH—O), 2.02-2.08 (m, 1H, —(CH$_2$)$_2$—CH—O—), 1.95-2.03 (m, 2H, >CH—CH$_2$) 1.19 (t, J=6.4 Hz, 3H, >CHCH$_2$—CH$_3$).

Example 33

A hydrochloride of V-55 4-benzyloxy-N-[2-hydroxy-2-(5-chloro-6-methoxynaphthalene-2-yl)]ethylpiperidine 2-bromoacetyl-5-chloro-6-methoxynaphthalene (5 mmol), 4-benzyloxypiperidine (4.51 mmol), and triethylamine (10 mmol) are dissolved in DMF (20 ml), and operated according to the general synthesis method one to obtain 1.89 g of a white solid, with yield of 91.3% (calculated based on 4-benzyloxypiperidine), MS (m/z): 424.0 [M+1]$^+$.

The white solid is reduced with aluminium isopropoxide according to the general synthesis method seven method A, and subjected to silica gel column chromatography (CH$_2$Cl$_2$:MeOH=300:1 to about 75:1). After formation of a hydrochloride, a hydrochloride of V-55 (1.25 g, with yield of 65.8%) is obtained.

Element analysis: C$_{25}$H$_{28}$ClNO$_3$.HCl (calculated value %: C, 64.94; H, 6.32; N, 3.03. found value %: C, 64.98; H, 6.31; N, 3.04).

MS: m/z 426.1 [M+1]$^+$.

Example 34

A hydrochloride of V-56 4-benzyloxy-N-[3-hydroxy-3-(5-chloro-6-methoxynaphthalene-2-yl)]propylpiperidine 3-chloropropionyl-5-chloro-6-methoxynaphthalene (5 mmol), 4-benzyloxypiperidine (4.51 mmol), and triethylamine (10 mmol) are dissolved in DMF (20 ml), and operated according to the general synthesis method six to obtain 1.92 g of a white solid, with yield of 89.7% (calculated according to 4-benzyloxypiperidine), MS (m/z): 438.0 [M+1]$^+$.

The white solid is reduced with aluminium isopropoxide according to the general synthesis method seven method A, and subjected to silica gel column chromatography (CH$_2$Cl$_2$:MeOH=300:1 to about 75:1). After formation of a hydrochloride, a hydrochloride of V-56 (1.20 g, with yield of 62.2%) is obtained.

Element analysis: C$_{26}$H$_{30}$ClNO$_3$.HCl (calculated value %: C, 65.54; H, 6.56; N, 2.94. found value %: C, 65.57; H, 6.56; N, 2.95).

MS: m/z 440.1 [M+1]$^+$.

Example 35

A hydrochloride of V-57 4-benzyloxy-N-[3-hydroxy-3-(benzothiophene-3-yl)]propylpiperidine 3-bromopropionyl chloride (28.4 mmol) is dissolved in chloroform (30 ml), thereto AlCl$_3$ (30.8 mmol) is added, and the reaction is stirred one hour at room temperature. AlCl$_3$ dissolves eventually, and the color of the solution is darkened to light brown. Temperature is controlled at <10° C., meanwhile slowly drop-adding chloroform (10 ml) solution of benzothiophene (23.7 mmol), and the reaction is allowed to warm to room temperature. After completion of addition, the reaction is stirred for one hour and the color of the reaction solution is darkened to brown. The reaction solution is poured into a mixture of hydrochloric acid (20 ml)/crashed ice (50 g) with stirring, and the color of the organic phase faded at light yellow to yellow. The organic phase is separated and washed with water (20 ml×3) until the aqueous phase is made neutral. After drying over anhydrous Na$_2$SO$_4$ overnight and filtering out the dessicant, the filter residue is washed with small amount of chloroform. The filtrate is evaporated to remove the solvent, to obtain the product as a light yellow oil. Column chromatography to separate the product (ethyl acetate:petroleum ether=1:400~1:60) as a light yellow oil, which solidified after standing, with yield of 60%.

3-bromopropionyl-3-benzothiophene (5 mmol), 4-benzyloxypiperidine (4.51 mmol), and triethylamine (10 mmol) are dissolved in DMF (20 ml), and operated according to the general synthesis method six to obtain 1.83 g of a white solid, with yield of 89.7% (calculated based on 4-benzyloxypiperidine), MS (m/z): 380.1 [M+1]$^+$.

The white solid is reduced with aluminium isopropoxide according to the general synthesis method seven method A, and subjected to silica gel column chromatography (CH$_2$Cl$_2$:MeOH=300:1 to about 75:1). After formation of a hydrochloride, a hydrochloride of V-57 (1.23 g, with yield of 65.4%) is obtained.

Element analysis: C$_{23}$H$_{27}$NO$_2$S.HCl (calculated value %: C, 72.40; H, 7.13; N, 3.67. found value %: C, 72.42; H, 7.12; N, 3.66).

MS: m/z 382.1 [M+1]$^+$.

Example 36

A hydrochloride of V-58 4-benzyloxy-N-[3-hydroxy-3-(indole-3-yl)]propylpiperidine 3-bromopropionyl chloride (28.4 mmol) is dissolved in chloroform (30 ml), thereto AlCl$_3$ (30.8 mmol) is added, and the reaction is stirred one hour at room temperature. AlCl$_3$ dissolves eventually, and the color of the solution is darkened to light brown. Temperature is controlled at <10° C., meanwhile slowly drop-adding chloroform (10 ml) solution of indole (23.7 mmol), and the reaction is allowed to warm to room temperature. After completion of addition, the reaction is stirred for one hour and the color of the reaction solution is darkened to brown. The reaction solution is poured into a mixture of hydrochloric acid (20 ml)/crashed ice (50 g) with stirring, and the color of the organic phase faded at light yellow to yellow. The organic phase is separated and washed with water (20 ml×3) until the aqueous phase is made neutral. After drying over anhydrous $Na_2SO_4$ overnight and filtering out the dessicant, the filter residue is washed with small amount of chloroform. The filtrate is evaporated to remove the solvent, to obtain the product as a light yellow oil. Column chromatography to separate the product (ethyl acetate:petroleum ether=1:400~1:60) as a light yellow oil, which solidified tiller standing, with yield of 51%.

3-bromopropionyl-3-indole (5 mmol), 4-benzyloxypiperidine (4.51 mmol), and triethylamine (10 mmol) are dissolved in DMF (20 ml), and operated according to the general synthesis method one to obtain 1.64 g of a white solid, with yield of 72.5% (calculated based on 4-benzyloxypiperidine), MS (m/z): 363.0 $[M+1]^+$.

The white solid is reduced with aluminium isopropoxide according to the general synthesis method seven method A, and subjected to silica gel column chromatography ($CH_2Cl_2$:MeOH=300:1 to about 75:1). After formation of a hydrochloride, a hydrochloride of V-58 (1.01 g, with yield of 60.5%) is obtained.

Element analysis: $C_{23}H_{28}N_2O_2 \cdot HCl$ (calculated value %: C, 75.79; H, 7.74; N, 7.69. found value %: C, 75.81; H, 7.75; N, 7.69).

MS: m/z 365.0 $[M+1]^+$

Example 37

A hydrochloride of V-59 (Threo-) and of V-60 (Erythro-) 4-(4-fluorobenzyloxy)-N-[1-methyl-2-hydroxy-2-(5-chloro-6-methoxynaphthalene-2-yl)] ethylpiperidine 2-bromo-1-(5-chloro-6-methoxynaphthalen-2-yl)-acetone (5 mmol), 4-(4-fluorobenzyloxy)piperidine (4.51 mmol), and triethylamine (10 mmol) are dissolved in DMF (20 ml), and operated according to the general synthesis method six to obtain 1.98 g of a white solid, with yield of 89.2% [calculated based on 4-(4-fluorobenzyloxy) piperidine], m.p=156.2-159.3° C. MS (m/z): 456.2 $[M+1]^+$.

The white solid is reduced with aluminium isopropoxide according to the general synthesis method seven method A, and subjected to silica gel column chromatography ($CH_2Cl_2$:MeOH=300:1 to about 75:1). After formation of a hydrochloride, a hydrochloride of threo-form V-59 (0.53 g, with yield of 26.6%) and a hydrochloride of erythro-form V-60 (0.48 g, with yield of 24.1%) are obtained, respectively.

V-59: m.p=203.2-206.1° C. MS (m/z): 458.2 $[M+1]^+$. $^1HNMR$ ($CDCl_3$): 8.25 (d, J=8.8 Hz, 1H, Ar—H), 7.88 (s, 1H, Ar—H), 7.80 (d, J=9.2 Hz, 1H, Ar—H), 7.66-7.73 (m, 2H, Ar—H), 7.31-7.39 (m, 4H, Ar—H), 4.72 (s, 2H, —O—$CH_2$-Ph), 4.10 (d, J=6.8 Hz, 1H, >CH—OH), 4.03 (s, 3H, —O—$CH_3$), 3.77-3.78 (m, 1H, >C$\overline{H}$—$CH_3$), 3.28-3.35 (m, 4H, —$\overline{N}$—$(CH_2)_2$—), 2.16-$\overline{2.44}$ (m, 4H, —$(CH_2)_2$—CH—$\overline{O}$—), 2.65-2.67 (m, 1H, —$(CH_2)_2$—$\overline{CH}$—O—), 1.00 (d, J=6.8 Hz, 3H, >CH—$\underline{CH_3}$).

V-60: m.p=205.5-209.8° C. MS (m/z): 458.0 $[M+1]^+$. $^1HNMR$ ($CDCl_3$): 8.09 (d, J=8.8 Hz, 1H, Ar—H), 7.87 (s, 1H, Ar—H), 7.66-7.73 (m, 2H, Ar—H), 7.51-7.53 (m, 3H, Ar—H), 7.23-7.37 (m, 2H, Ar—H), 4.50 (s, 2H, —O—$CH_2$-Ph), 4.10 (d, J=2.4 Hz, >CH—OH), 4.01 (s, 3H, —O—$\overline{CH_3}$), 3.79-3.81 (m, 1H, >C$\overline{H}$—$CH_3$), 3.30-3.32 (m, 4H, —$\overline{N}$—$(CH_2)_2$—), 2.40-2.60 (m, 4H, —$(CH_2)_2$—CH—O), 2.02-2.08 (m, 1H, —$(CH_2)_2$—$\overline{CH}$—O—), 1.19 (d, J=6.4 Hz, 3H, >CH—$\underline{CH_3}$).

Example 38

A hydrochloride of V-61 (Threo-) and of V-62 (Erythro-) 4-(4-fluorobenzyl amino)-N-[1-methyl-2-hydroxy-2-(5-chloro-6-methoxynaphthalene-2-yl)] ethylpiperidine 2-bromo-1-(5-chloro-6-methoxynaphthalen-2-yl)-acetone (5 mmol). 4-(N-p-toluenesulfonyl-4-fluorobenzylamino)piperidine (4.51 mmol), and triethylamine (10 mmol) are dissolved in DMF (20 ml), and operated according to the general synthesis method six to obtain 1.96 g of a white solid, with yield of 71.5% [calculated based on 4-(N-p-Toluenesulfonyl-4-fluoro benzyl amino) piperidin]. MS (m/z): 610.0 $[M+1]^+$.

The white solid is dissolved in ethanol (20 ml), thereto 40% NaOH aqueous solution (4 ml) is added, and the reaction is refluxed for four hours. After concentrating to dryness, ethyl acetate (20 ml) and water (10 ml) are added for extracting. After separating, diving concentrating, and funning a hydrochloride in hydrochloric acid-ethanol, 1.46 g of the produce as a white solid is obtained, with yield of 100%.

The white solid is reduced with aluminium isopropoxide according to the general synthesis method seven method A, and subjected to silica gel column chromatography ($CH_2Cl_2$:MeOH=300:1 to about 75:1). After formation of a hydrochloride, a hydrochloride of threo-form V-61 (0.50 g, with yield of 21.5%) and a hydrochloride of erythro-form V-62 (0.52 g, with yield of 25.6%) are obtained, respectively.

V-61: MS (m/z): 457.2 $[M+1]^+$. $^1HNMR$ ($CDCl_3$): 8.20 (d, J=8.6 Hz, 1H, Ar—H), 7.84 (s, 1H, Ar—H), 7.80 (d, J=9.0 Hz, 1H, Ar—H), 7.66-7.73 (m, 2H, Ar—H), 7.25-7.31 (m, 4H, Ar—H), 3.92 (s, 2H, —NH—$CH_2$-Ph), 4.08 (d, J=6.8 Hz, 1H, >CH—OH), 4.00 (s, 3H, —O—$CH_3$), 3.75-3.77 (m, 1H, >C$\overline{H}$—$CH_3$), 3.26-3.35 (m, 4H, —$\overline{N}$—$(CH_2)_2$—), 2.16-2.44 (m, 4H, —$(CH_2)_2$—CH—NH—), 2.$\overline{42}$-$\overline{2.47}$ (m, 1H, —$(CH_2)_2$—$\overline{CH}$—$\overline{NH}$—), 1.00 (d, J=6.8 Hz, 3H, >CH—$\underline{CH_3}$).

V-62: MS (m/z): 457.2 $[M+1]^+$. $^1HNMR$ ($CDCl_3$): 8.12 (d, J=8.8 Hz, 1H, Ar—H), 7.87 (s, 1H, Ar—H), 7.78 (d, J=9.0 Hz, 1H, Ar—H), 7.63-7.72 (m, 2H, Ar—H), 7.21-7.26 (m, 4H, Ar—H), 3.85 (s, 2H, —NH—$CH_2$-Ph), 4.10 (d, J=2.4 Hz, >CH—OH), 4.01 (s, 3H, —O—$\overline{CH_3}$), 3.79-3.81 (m, 1H, >C$\overline{H}$—$CH_3$), 3.31-3.33 (m, 4H, —$\overline{N}$—$(CH_2)_2$—), 2.40-2.50 (m, 4H, —$(CH_2)_2$—CH—NH), 2.$\overline{00}$-$\overline{2.06}$ (m, 1H, —$(CH_2)_2$—C$\overline{H}$—$\overline{NH}$—), 1.10 (d, J=6.4 Hz, 3H, >CH—$\underline{CH_3}$).

Example 39

A hydrochloride of V-63 4-benzyl-4-methoxy-N-[3-hydroxy-3-(5-chloro-6-methoxynaphthalene-2-yl)] propylpiperidine 3-chloro-1-(5-chloro-6-methoxynaphthalene-2-yl)-acetone (10 mmol), 4-benzyl-4-methoxypiperidine (8 mmol), and triethylamine (30 mmol) are dissolved in DMF (50 mL), and operated according to the general synthesis method one to obtain 3.13 g of a white solid, with yield of 82.0% (calculated based on 4-benzyl-4-methoxypiperidine), MS (m/z): 453.0 $[M+1]^+$.

The white solid is dissolved in methanol (30 mL), reduced with $NaBH_4$ according to the general synthesis method seven method B, and subjected to silica gel column chromatography ($CH_2Cl_2$:MeOH=300:1 to about 75:1). After formation of a hydrochloride, a hydrochloride of V-63 (2.32 g, with yield of 70.6%) is obtained.

Element analysis: $C_{27}H_{33}Cl_2NO_3$ (calculated value %: C, 66.12; H, 6.78; N, 2.86. found value %: C, 66.20; H, 6.80; N, 2.87).

MS: m/z 455.1 $[M+1]^+$.

Example 40

| Tablet: | the compounds of Examples 1-39 | 10 mg |
|---|---|---|
| | Sucrose | 150 mg |
| | Corn starch | 38 mg |
| | Calcium stearate | 2 mg |

The formulating method: the active ingredient is mixed with sucrose and corn starch. The mixture is moistened by adding water, stirred homogeneously, dried, crashed and sieved. Thereto calcium stearate is added, and then the resulted mixture is mixed homogeneously and pressed to be a tablet. Each tablet has a weight of 200 mg and has 10 mg of the active ingredient.

Example 41

| Injection: | The compounds of Examples 1-39 | 20 mg |
|---|---|---|
| | Water for injection | 80 mg |

The formulating method: the active ingredient is dissolved in water for injection, mixed homogeneously and filtered. The obtained solution is packaged into ampoule under sterilized conditions. Each bottle contains 10 mg solution and has 2 mg of the active ingredient.

Example 42

Anti-Depression Activity of the Compound

1. The Inhibition Activity of the Compound on Uptake of 5-Serotonin (5-HT), Norepinephrine (NA) and Dopamine (DA) by Brain Synaptosomes:

The research method on the reuptaking of monoamine neurotransmitter by brain synaptosomes reported by (Biochem Pharmacol 1973, 22, 311-322) is used, which is one of the important means for the pharmacological study of central nerve system internationally. The method can be used not only to study the function mechanism of drugs, but also to screen new drugs for this purpose. The present inventor uses the research method of the reuptake of monoamine neurotransmitters 5-HT, NA and DA by brain synaptosomes, using venlafaxine as an effective dual reuptake inhibitor of 5-HT and NA, and DOV 21947 as a triple reuptake inhibitor of 5-HT, NA and DA as positive control; and studies the effect of the compound of the present invention on inhibiting brain synaptosomes from reuptake of 5-HT, NA and DA. The method comprises the following steps:

(1) Preparation of Synaptosomes of a Rat Brain:

Male SD rat was killed by cervical dislocation, and then the head was cut and the brain was removed therefrom and dropped into ice rapidly; separating the relevant brain tissues (taking prefrontal cortex for the $[^3H]5$-HT and $[^3H]NA$ reuptake experiment, and taking striatum for the $[^3H]DA$ reuptake experiment). After weighing, adding 10 time (V/W) a freezed 0.32 mol/L sucrose liquid, and performing an electric homogenization with a glass-teflon: the homogenate is subjected to a centrifugal force at 1000 g× for 10 mins at 4° C.; taking supernatant, and the supernatant is subjected to a centrifugal force at 17000 g× for 20 mins at 4° C.; taking precipitate, and the precipitate is suspended with 30 times the volume of KRH Buffer (125 mM NaCl, 4.8 mM KCl, 1.2 mM $CaCl_2$, 1.2 mM $MgSO_4$, 1.0 mM $KH_2PO_4$, 22 mM $HaHCO_3$, 25 mM HEPES, 10 mM Glucose, 10 μM Pargyline, 0.2 mg/ml Ascorbic Acid), and placed in ice bath for use (wherein the cortex for the NA reuptake experiment is suspended with 20 times the volume).

(2) The $[^3H]5$-HT/NA/DA Reuptake Experiment:

With reference to the documents (a. Biochem Pharmacol 1973, 22, 311-322, b. Methods in Neurochemistry, Vol. 2, New York: Marcel Dakker, 1972, 1-52), a stock liquid of the sample to be detected is taken out just before testing, thawed, and diluted by KRH Buffer to 10 μmol/L, of which 50 μl is added to the 500 μl of total reaction system, i.e., to reach a final concentration of 10 μmol/L. Thereto 50 μl of suspension of synaptosome membrane is additionally added and mixed evenly, and incubated in a water bath at 37° C. for 30 mins; thereafter adding 10 nmol/L of $[^3H]5$-HT (50 nmol/L $[^3]DA$ or 60 nmol/L $[^3]NA$), and incubating in a water bath at 37° C. for 10 mins; then taking out immediately and putting into 2 ml of freezed 150 mmol/L of Tris-HCl buffer to terminate the reaction, vacuum filtering to collect the sample on a round fiber glass film, washing the film three times with the freezed Tris-HCl buffer; taking off the filter film, and the filter film is placed and dried in a far-infrared oven for 15 mins, then placed in EP tube, thereto 1.5 ml of scintillation solution is added, and a detection is performed using liquid scintillation counter after overnight. Solvent control total binding tube and non specific binding tube are not added with the sample to be detected. The total binding tube is added with 50 μl solvent, the non specific binding tube for the $[^3H]5$-HT reuptake experiment is added with 600 μmol/L of Cocaine, the non specific binding tube for the $[^3H]NA$ reuptake experiment is added with 100 μmol/L of DOV 21947, and the non specific binding tube for the $[^3H]DA$ reuptake experiment is added with 600 μmol/L of Cocaine.

(3) The result: at the condition of the same concentrations (0.1 mmol/L for both the control drug and the drug to be detected), the commercial antidepressant venlafaxine and the anti-depression II stage clinical compound DOV 21947 are used as positive control, and the test results of reuptake inhibition effect on 5-HT, NA and DA is shown in Table 2.

TABLE 2

The inhibition effect of the compounds on reuptake of 5-serotonin (5-HT), norepinephrine (NA) and dopamine (DA) by brain synaptosomes

| Compound | Inhibition of reuptake of 5-HT | Inhibition of reuptake of NA | Inhibition of reuptake of DA |
|---|---|---|---|
| V-2 | 105.6 ± 0.9 | 65.3 ± 6.7 | 93.1 ± 2.0*# |
| V-14 | 94.9 ± 1.2*# | 93.0 ± 20.8* | 91.0 ± 0.9*# |

TABLE 2-continued

The inhibition effect of the compounds on reuptake of 5-serotonin
(5-HT), norepinephrine (NA) and dopamine (DA) by brain synaptosomes

| Compound | Inhibition of reuptake of 5-HT | Inhibition of reuptake of NA | Inhibition of reuptake of DA |
|---|---|---|---|
| V-32 | 104.4 ± 2.0 | 36.6 ± 19.1 | 92.4 ± 7.6* |
| V-34 | 106.3 ± 2.3 | 18.8 ± 13.4[#] | 99.1 ± 4.3* |
| V-38 | 107.0 ± 0.5 | 87.4 ± 5.5*[#] | 99.6 ± 2.9* |
| V-40 | 99.5 ± 1.6* | 62.6 ± 15.3 | 50.7 ± 21.8 |
| V-50 | 91.8 ± 1.6*[#] | 41.8 ± 7.3 | 23.1 ± 16.8[#] |
| venlafaxine | 106.9 ± 1.7 | 46.4 ± 4.6 | 48.6 ± 4.1 |
| DOV 21947 | 108.6 ± 3.8 | 61.9 ± 6.0 | 104.1 ± 4.2* |

*as compared with venlafaxine, $P < 0.05$.
[#]as compared with DOV 21047, $P < 0.05$ When the concentration is 10 μmol/L, four compounds, i.e., V-2, V-14, V-32, V-38 have stronger inhibiting activity on the reuptake of 5-HT, NA and DA, the effectiveness is equivalent to that of venlafaxine and DOV21947.

2. The In Vivo Anti-Depression Effect of Compound V-14:

Using tail suspension test in "learned despair", and "immobility" in forced swimming test of mice, and using venlafaxine as positive control, a preliminary studies were conducted on the in vivo anti-depression effect of V-14 that is potent in inhibiting triple-reuptake (5-HT, NA and DA).

The result is shown in Table 3:

TABLE 3

The result of the preferable compounds
in the swimming test of mice

| Compound | Dosage (mg/kg) | Immobility time (s) |
|---|---|---|
| CMC—Nn | 20 ml/kg | 138 ± 30.1 |
| venlafaxine | 18.24 | 80.8 ± 46.8* |
| | 9.12 | 77.4 ± 47.2** |
| | 4.56 | 57.1 ± 37.8** |
| V-14 | 27.6 | 74.9 ± 37.8** |
| | 13.8 | 82.1 ± 62.0* |
| | 6.9 | 52.8 ± 32.0** |

*as compared with positive control, $P < 0.5$, exhibiting significant difference.
**as compared with positive control, $P < 0.05$, exhibiting extremely significant difference.

In the "immobility" in forced swimming test of mice, V-14 obviously shortens the period of stopping swimming and immobility of mice in water due to despair, a dosage of 27.6 mg/kg has the similar effect (74.9±37.8 s) to that of the positive venlafaxine at an equivalent molar amount of 18.24 mg/kg (80.8±46.8 s), and is significantly different from the control group, which means that V-14 has strong in vivo anti-depression activity, and the effect is similar to that of venlafaxine.

3. Acute toxicity: a preliminary screening is performed using the method reported in Modern experimental methods in pharmacology by ZHANG Juntian, and subjected to a Bliss-statistics using a single dosage of $LD_{50i}$ of V-14 to mice being 1150 mg/kg.

4. A Bacterial Reverse Mutation Assay Using Compound V-14

Strains: *Salmonella typhimurium* histidine auxotroph mutant $TA_{97}$, $TA_{98}$, $TA_{100}$ and $TA_{102}$.

The experimental method: the method reported in Maron D M et al: (1983) Mutay Res. 113, 173-216 is used;

The experimental result: the experiment comprises two parts: $-S_9$ and $+S_9$. Both 5000 μg/dish of $TA_{95}$ in non-$S_9$ testing system and 5000 μg/dish of $TA_{97}$ in $S_9$ added testing system have bacteriostatic effect. Other dosages do not have a bacteriostatic effect to all strains, and provide a good background of growth. All tested dosages do not significantly increase the amounts of reverse mutation on strain in experimental systems with or without $S_9$, and the Ames test is negative.

We claim:

1. A compound or a tree base or a salt thereof selected from:
   V-1 Threo-4-benzyl-N-[1-methyl-2-hydroxy-2-(5-chloro-6-methoxynaphthalene-2-yl)]ethylpiperidine;
   V-2 Erythro-4-benzyl-N-[1-methyl-2-hydroxy-2-(5-chloro-6-methoxynaphthalene-2-yl)]ethylpiperidine;
   V-5 Threo-4-benzyl-N-[1-ethyl-2-hydroxy-2-(5-chloro-6-methoxynaphthalene-2-yl)]ethylpiperidine;
   V-6 Erythro-4-benzyl-N-[1-ethyl-2-hydroxy-2-(5-chloro-6-methoxynaphthalene-2-yl)]ethylpiperidine;
   V-11 Threo-4-(4-fluorobenzyl)-N-[1-methyl-2-hydroxy-2-(5-chloro-6-methoxynaphthalene-2-yl)]ethylpiperidine,
   V-12 Erythro-4-(4-fluorobenzyl)-N-[1-methyl-2-hydroxy-2-(5-chloro-6-methoxynaphthalene-2-yl)]ethylpiperidine;
   V-13 Threo-4-benzyl-4-hydroxy-N-[1-methyl-2-hydroxy-2-(5-chloro-6-methoxynaphthalene-2-yl)]ethylpiperidine;
   V-14 Erythro-4-benzyl-4-hydroxy-N-[1-methyl-2-hydroxy-2-(5-chloro-6-methoxynaphthalene-2-yl)]ethylpiperidine;
   V-15 Threo-4-benzyl-4-hydroxy-N-[1-ethyl-2-hydroxy-2-(5-chloro-6-methoxynaphthalene-2-yl)]ethylpiperidine;
   V-16 Erythro-4-benzyl-4-hydroxy-N-[1-ethyl-2-hydroxy-2-(5-chloro-6-methoxynaphthalene-2-yl)]ethylpiperidine;
   V-21 Threo-4-(4-chlorobenzyl)-4-hydroxy-N-[1-methyl-2-hydroxy-2-(5-chloro-6-methoxynaphthalene-2-yl)]ethylpiperidine;
   V-22 4-(4-chlorobenzyl)-4-hydroxy-N-[1-methyl-2-hydroxy-2-(5-chloro-6-methoxynaphthalene-2-yl)]ethylpiperidine;
   V-23 Threo-4-(4-fluorobenzyl)-4-hydroxy-N-[1-methyl-2-hydroxy-2-(5-chloro-6-methoxynaphthalene-2-yl)]ethylpiperidine;
   V-24 Erythro-4-(4-fluorobenzyl)-4-hydroxy-N-[1-methyl-2-hydroxy-2-(5-chloro-6-methoxynaphthalene-2-yl)]ethylpiperidine;
   V-25 Threo-4-(3,4-dichlorobenzyl)-methylene-N-[1-methyl-2-hydroxy-2-(5-chloro-(6-methoxynaphthalene-2-yl)]ethylpiperidine;

V-26 Erythro-4-(3,4-dichlorobenzyl)-methylene-N-[1-methyl-2-hydroxy-2-(5-chloro-6-methoxynaphthalene-2-yl)]ethylpiperidine;

V-29 Threo-4-(3,4-dichlorobenzyl)-methylene-N-[1-ethyl-2-hydroxy-2-(5-chloro-6-methoxynaphthalene-2-yl)]ethylpiperidine;

V-30 4-(3,4-dichlorobenzyl)-methylene-N-[1-ethyl-2-hydroxy-2-(5-chloro-6-methoxynaphthalene-2-yl)]ethylpiperidine;

V-31 4-benzyl-methylene-N-[2-hydroxy-2-(5-chloro-6-methoxynaphthalene-2-yl)]ethylpiperidine;

V-32 4-benzyl-methylene-N-[3-hydroxy-3-(5-chloro-6-methoxynaphthalene-2-yl)]propylpiperidine;

V-33 Threo-4-(4-fluorobenzyl)-methylene-N-[1-ethyl-2-hydroxy-2-(5-chloro-6-methoxynaphthalene-2-yl)]ethylpiperidine;

V-34 Erythro-4-(4-fluorobenzyl)-methylene-N-[1-ethyl-2-hydroxy-2-(5-chloro-(6-methoxynaphthalene-2-yl)]ethylpiperidine;

V-35 Threo-4-(4-chlorobenzyl)-methylene-N-[1-ethyl-2-hydroxy-2-(5-chloro-6-methoxynaphthalene-2-yl)]ethylpiperidine;

V-36 Erythro-4-(4-chlorobenzyl)-methylene-N-[1-ethyl-2-hydroxy-2-(5-chloro-6-methoxynaphthalene-2-yl)]ethylpiperidine;

V-37 Threo-4-benzyl-methylene-N-[1-ethyl-2-hydroxy-2-(5-chloro-6-methoxynaphthalene-2-yl)]ethylpiperidine;

V-38 Erythro-4-benzyl-methylene-N-[1-ethyl-2-hydroxy-2-(5-chloro-6-methoxynaphthalene-2-yl)]ethylpiperidine;

V-39 Threo-4-benzyl-N-[1-methyl-2-hydroxy-2-(5-chloro-6-methoxynaphthalene-2-yl)]ethyl-1,2,3,6-tetrahydropyridine;

V-40 Erythro-4-benzyl-N-[1-methyl-2-hydroxy-2-(5-chloro-6-methoxynaphthalene-2-yl)]ethyl-1,2,3,6-tetrahydropyridine;

V-43 Threo-4-benzyl-N-[1-ethyl-2-hydroxy-2-(5-chloro-6-methoxynaphthalene-2-yl)]ethyl-1,2,3,6-tetrahydropyridine;

V-44 Erythro-4-benzyl-N-[1-ethyl-2-hydroxy-2-(5-chloro-6-methoxynaphthalene-2-yl)]ethyl-1,2,3,6-tetrahydropyridine;

V-47 Threo-4-(4-fluorobenzyl)-N-[1-methyl-2-hydroxy-2-(5-chloro-6-methoxynaphthalene-2-yl)]ethyl-1,2,3,6-tetrahydropyridine;

V-48 Erythro-4-(4-fluorobenzyl)-N-[1-methyl-2-hydroxy-2-(5-chloro-6-methoxynaphthalene-2-yl)]ethyl-1,2,3,6-tetrahydropyridine.

2. A composition comprising a therapeutically effective amount of the compound according to claim 1 or a free base or a salt thereof and a pharmaceutically acceptable carrier for the treatment of depression.

3. The composition according to claim 2, wherein the salt is hydrochloride, hydrobromide, sulfate, trifluoroacetate or methanesulfonate.

4. A method of manufacturing a medicament for the treatment of depression, the method comprising combining a therapeutically effective amount of the compound according to claim 1 or a free base or a salt thereof and a pharmaceutically acceptable carrier.

5. The method of claim 4, wherein the salt is hydrochloride, hydrobromide, sulfate, trifluoroacetate or methanesulfonate.

* * * * *